(12) United States Patent
Ouyang et al.

(10) Patent No.: US 7,560,920 B1
(45) Date of Patent: Jul. 14, 2009

(54) APPARATUS AND METHOD FOR EDDY-CURRENT SCANNING OF A SURFACE TO DETECT CRACKS AND OTHER DEFECTS

(75) Inventors: Tianhe Ouyang, Superior, CO (US); Yushi Sun, Superior, CO (US)

(73) Assignee: Innovative Materials Testing Technologies, Inc., Superior, CO (US)

( * ) Notice: Subject to any disclaimer, the term of this patent is extended or adjusted under 35 U.S.C. 154(b) by 157 days.

(21) Appl. No.: 11/553,996

(22) Filed: Oct. 28, 2006

Related U.S. Application Data

(60) Provisional application No. 60/731,321, filed on Oct. 28, 2005.

(51) Int. Cl.
*G01N 27/90* (2006.01)
*G01R 33/12* (2006.01)

(52) U.S. Cl. .................. 324/242; 324/240; 324/243

(58) Field of Classification Search .................. 324/202, 324/222, 225, 228, 229, 233, 239, 240, 242, 324/243
See application file for complete search history.

(56) References Cited

U.S. PATENT DOCUMENTS

| | | | |
|---|---|---|---|
| 2,573,799 | A | 11/1951 | MacLean |
| 2,610,230 | A | 9/1952 | Wiegand |
| 3,249,778 | A | 5/1966 | McDougal |
| 3,996,510 | A | 12/1976 | Guichard |
| 4,271,393 | A | 6/1981 | Hansen et al. |
| 4,495,466 | A | 1/1985 | Lakin |
| 4,496,904 | A | 1/1985 | Harrison |
| 4,797,614 | A | 1/1989 | Nelson |
| 4,855,677 | A | 8/1989 | Clark, Jr. et al. |
| 5,111,412 | A | * 5/1992 | Tornblom .................. 702/38 |

(Continued)

FOREIGN PATENT DOCUMENTS

CA 1 208 291 7/1986

(Continued)

OTHER PUBLICATIONS

Atherton, D. A., et al., "Finite-Element Calculation for Shields in Remote-Field Eddy Current Tools", "Materials Evaluation", Sep. 1989, pp. 1084-1088, vol. 47.

(Continued)

*Primary Examiner*—Kenneth J Whittington
(74) *Attorney, Agent, or Firm*—Charles A. Lemaire; Lemaire Patent Law Firm, P.L.L.C.

(57) ABSTRACT

An apparatus having a plurality of coils (e.g., numerous thin-film coils formed in an array on a flex circuit), each coil acting as an excitation unit that generates an alternating excitation magnetic signal; and as a sensor configured to detect an eddy-current signal's phase and amplitude changes relative to the excitation magnetic signal. In some embodiments, the apparatus electronically scans a surface (e.g., of a metal plate) by successively switching to individual ones of the plurality of excitation/sensing coils (using, e.g., an analog multiplexer) without physical movement in order to detect anomalous signal changes in a manner that reduces signal changes due to probe lift-off relative to the surface. In some embodiments, the coils are placed across a large area of interest, for inspection of a large surface area in a few seconds without moving the apparatus. This can provide high-sensitivity detection and an accurate indication of flaw locations.

37 Claims, 12 Drawing Sheets

U.S. PATENT DOCUMENTS

| | | | |
|---|---|---|---|
| 5,182,513 A | | 1/1993 | Young et al. |
| 5,264,733 A | | 11/1993 | Tigges |
| 5,345,514 A | | 9/1994 | Mahdavieh et al. |
| 5,389,876 A | | 2/1995 | Hedengren et al. |
| 5,399,968 A | | 3/1995 | Sheppard et al. |
| 5,414,356 A | | 5/1995 | Yoshimura et al. |
| 5,485,084 A | * | 1/1996 | Duncan et al. ............. 324/225 |
| 5,554,933 A | | 9/1996 | Logue |
| 5,572,120 A | | 11/1996 | Takaishi et al. |
| 5,648,721 A | | 7/1997 | Wincheski et al. |
| 5,659,248 A | * | 8/1997 | Hedengren et al. .......... 324/242 |
| 5,793,206 A | | 8/1998 | Goldfine et al. |
| 5,955,954 A | | 9/1999 | Keller |
| 6,002,251 A | | 12/1999 | Sun |
| 6,014,024 A | | 1/2000 | Hockey et al. |
| 6,144,206 A | | 11/2000 | Goldfine et al. |
| 6,188,218 B1 | | 2/2001 | Goldfine et al. |
| 6,252,398 B1 | | 6/2001 | Goldfine et al. |
| 6,377,039 B1 | | 4/2002 | Goldfine et al. |
| 6,380,747 B1 | | 4/2002 | Goldfine et al. |
| 6,420,867 B1 | | 7/2002 | Goldfine et al. |
| 6,636,037 B1 | | 10/2003 | Ou-Yang |
| 6,727,691 B2 | | 4/2004 | Goldfine et al. |
| 6,781,387 B2 | | 8/2004 | Goldfine et al. |
| 6,784,662 B2 | | 8/2004 | Schlicker et al. |
| 6,798,198 B2 | | 9/2004 | Tsukernik et al. |
| 6,885,190 B2 | * | 4/2005 | Lehman et al. ............. 324/230 |
| 6,952,095 B1 | | 10/2005 | Goldfine et al. |
| 6,992,482 B2 | | 1/2006 | Shay et al. |
| 6,995,557 B2 | | 2/2006 | Goldfine et al. |
| 7,095,224 B2 | | 8/2006 | Goldfine et al. |
| 7,106,055 B2 | | 9/2006 | Goldfine et al. |
| 7,161,350 B2 | | 1/2007 | Goldfine et al. |
| 7,161,351 B2 | | 1/2007 | Goldfine et al. |
| 7,183,764 B2 | | 2/2007 | Goldfine et al. |
| 7,188,532 B2 | | 3/2007 | Goldfine et al. |
| 7,280,940 B2 | | 10/2007 | Goldfine et al. |
| 7,289,913 B2 | | 10/2007 | Schlicker et al. |
| 7,301,335 B2 | | 11/2007 | Sun et al. |
| 7,348,771 B2 | | 3/2008 | Goldfine et al. |
| 7,385,392 B2 | | 6/2008 | Schlicker et al. |
| 7,411,390 B2 | | 8/2008 | Goldfine et al. |
| 7,451,639 B2 | | 11/2008 | Goldfine et al. |
| 7,451,657 B2 | | 11/2008 | Goldfine et al. |
| 2003/0164700 A1 | | 9/2003 | Goldfine et al. |
| 2003/0173958 A1 | | 9/2003 | Goldfine et al. |
| 2004/0004475 A1 | | 1/2004 | Goldfine et al. |
| 2004/0056654 A1 | | 3/2004 | Goldfine et al. |
| 2004/0225474 A1 | | 11/2004 | Goldfine et al. |
| 2005/0007106 A1 | | 1/2005 | Goldfine et al. |
| 2005/0017713 A1 | | 1/2005 | Goldfine et al. |
| 2005/0127908 A1 | | 6/2005 | Goldfine et al. |
| 2005/0248339 A1 | | 11/2005 | Goldfine et al. |
| 2006/0009865 A1 | | 1/2006 | Goldfine et al. |
| 2006/0022669 A1 | | 2/2006 | Nygaard |
| 2006/0076952 A9 | | 4/2006 | Goldfine et al. |

FOREIGN PATENT DOCUMENTS

| | | | |
|---|---|---|---|
| CN | ZL 90105697 | | 9/1993 |
| JP | 59-162448 | | 9/1984 |
| WO | WO 2007015705 A2 | | 2/2007 |

OTHER PUBLICATIONS

Chen, M. J., et al., "A Finite Element Prediction of Possible Application of Pulse Excitation in Remote Field Eddy Current Nondestructive Insp", "International Journal of Applied Electromagnetics in Materials", 1991, pp. 217-220, vol. 2.

Chen, M., et al., "Pulsed RFEC Probe Response", "IEEE Transaction on Magnetics", Mar. 1992, pp. 1430-1433, vol. 28, No. 2.

Lin, H.Y., et al., "Application of 'Zoom-In' Technique in 3D Remote Field Eddy Current Effect Calculation", "IEEE Trans. on Magnetics", Mar. 1990, pp. 881-884, vol. 26, No. 2.

Lord, W., et al., "A Finite Element Study of the Remote Field Eddy Current Phenomenon", "IEEE Transaction on Magnetics", Jan. 1988, pp. 435-438, vol. 24, No. 1.

Lord, W., et al., "Physics of Remote Field Eddy Current Effect", "Review of Progress in Quantitative Nondestructive Evaluation", 1988, pp. 165-172, vol. 7.

Schmidt, Thomas R., "The Remote Field Eddy Current Technique", "Materials Evaluation,", Feb. 1984, pp. 225-230, vol. 42.

Sun, Y., et al., "3-D Finite Element Modeling of the Remote Field Eddy Current Effect", "Review of Progress in QNDE", 1990, pp. 319-326, vol. 9.

Sun, Y. S., et al., "A Remote Field Eddy Current NDT Probe for the Inspection of Metallic Plates", "Material Evaluation", Apr. 1996, pp. 510-512.

Sun, Y. S., et al., "Computer Animated Presentation Visualizing the Phenomena in Remote Field Eddy Current Non-destructive Testing", "Electromagnetic Forces and Applications", 1992, pp. 203-206.

Sun, Y. S., et al., "Crack Modeling Problem in Eddy Current Nondestructive Testing", "Electromagnetic Phenomena and Computation Techniques", 1992, pp. 173-182.

Sun, Yushi, et al., "Efforts Towards Gaining a Better Understanding of the Remote Field Eddy Current Phenomenon and Expanding its Application", "IEEE Transaction on Magnetics", 1996, pp. 1589-1592, vol. 22, No. 3.

Sun, Yu Shi, et al., "Finite Element Modelling and Physics of Remote Field Eddy Current Responses for Axially Aligned Cracks", "IEEE Transaction on Magnetics", Jul. 1992, pp. 1941-1947, vol. 28, No. 4.

Sun, Y. S., et al., "Improvement in Remote-Field Eddy Current Probe Structure", "Materials Evaluation", May 1992, pp. 600-604, vol. 50.

Sun, Y. S., et al., "Inspection of Metallic Plates Using a Novel Remote Field Eddy Current NDT Probe", "Review of Progress in QNDE", 1996, pp. 1137-1144, vol. 15.

Sun, Y. S., et al., "Motion Induced Remote Field Eddy Current Effect in a Magnetostatic Non-destructive Testing Tool", "IEEE Transaction on Magnetics", Sep. 1994, pp. 3304-3307, vol. 30, No. 5.

Sun, Y. S., et al., "Progress in Developing RFEC Probe for Tank Bottom Inspection", "presented on ASNT's 1996 Spring Conference ASNT, Norfolk, VA", Mar. 18-21, 1996.

Sun, Y. S., "Finite-Element Study of Diffusion Energy Flow in Low-Frequency Eddy Current Fields", "Materials Evaluation", 1989, pp. 87-92, vol. 47.

Von Rosen, E., et al., "Effect of Shielding and Exciter Coil Tilt on the Remote-Field Effect", "Materials Evaluation", Jan. 1993, pp. 66-71, vol. 51.

* cited by examiner

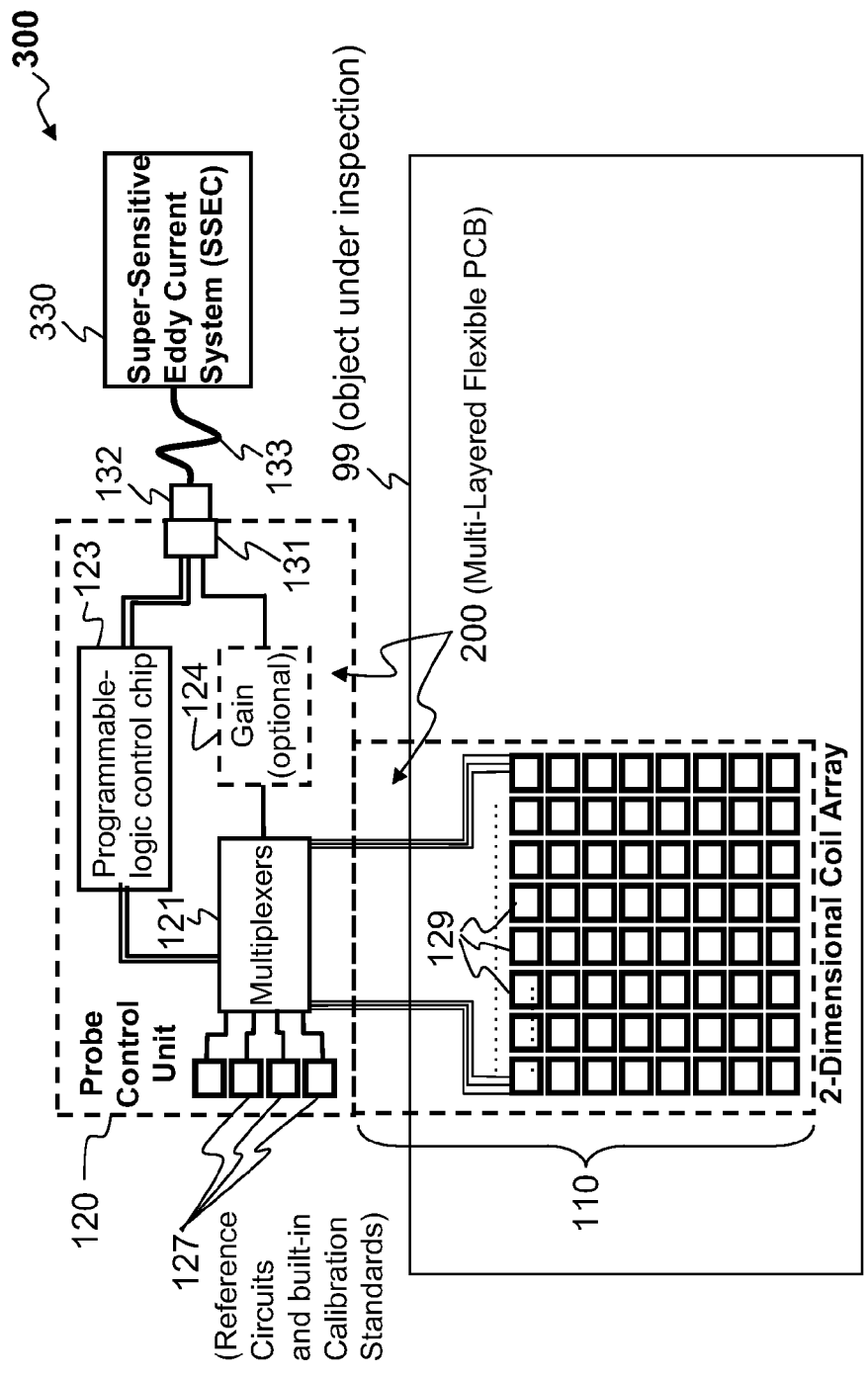
FIG. 3   Diagram for Magnetic Carpet Probe Model #1 (MCP-1) Working at Differential Mode

APPARATUS AND METHOD FOR EDDY-CURRENT SCANNING OF A SURFACE TO DETECT CRACKS AND OTHER DEFECTS

REFERENCE TO RELATED APPLICATIONS

This application claims benefit of U.S. Provisional Patent Application Ser. No. 60/731,321, filed on Oct. 28, 2005 and titled "APPARATUS AND METHOD FOR EDDY-CURRENT SCANNING OF A SURFACE TO DETECT CRACKS AND OTHER DEFECTS," which is incorporated herein by reference in its entirety. This application is also related to U.S. patent application Ser. No. 11/114,507, filed Apr. 25, 2005 and titled "APPARATUS AND METHOD FOR EDDY-CURRENT MAGNETIC SCANNING A SURFACE TO DETECT SUB-SURFACE CRACKS AROUND A BOUNDARY," which is incorporated herein by reference in its entirety.

STATEMENT REGARDING FEDERALLY SPONSORED RESEARCH OR DEVELOPMENT

This invention was made with Government support under Contract No. DTFACT-04-00013 awarded by the Federal Aviation Administration (FAA). The Government has certain rights in the invention.

FIELD OF THE INVENTION

The present invention relates to non-destructive eddy-current testing, and more particularly, to electromagnetic probes with a plurality of coils that provide both an excitation function and a sensing function.

BACKGROUND OF THE INVENTION

Magnetic fields create eddy currents within certain types of materials in objects in their path. The eddy currents in turn affect the magnetic field as observed from outside the objects. Cracks, discontinuities, holes, and changes in the material content all affect the eddy-current flow within an object and also affect the magnetic field external to the object. Accordingly, magnetic fields can be used to scan materials to determine if the materials contain inconsistencies and anomalies (such as cracks or corrosion) that affect the magnetic field.

Remote-field eddy-current techniques can be used to scan materials. Remote-field eddy-current techniques (RFEC) generally involve detecting magnetic-field changes caused by anomalies on a surface of, and/or hidden in, a structure due to the RFEC technology's double-wall-transmission feature.

In contrast, conventional eddy-current (EC) techniques generally involve detecting magnetic-field changes caused by anomalies on surface and near-surface areas. This is because the direct coupling is dominating in conventional eddy-current technique. There are not separate drive and pickup coils/units used in EC absolute and differential modes. In the reflection mode, in spite of the geometrical separation of the two coils/units, the direct coupling of excitation unit(s) and sensor unit(s) is still dominating. Generally, the magnetic separation of drive and pickup units, using shields and magnetic circuits, for an RFEC probe is greater than that of an EC probe working in reflection mode. Changes to an observed RFEC or conventional EC signal can be caused by undesirable anomalies, even those hidden in a surface, such as cracks, voids, internal or surface corrosion, embedded foreign objects, alloy-composition changes, etc., as well as by expected inherent features of the object being examined, such as joints and fasteners.

U.S. Pat. No. 6,636,037 issued to Tianhe OUYANG on Oct. 21, 2003, is titled "Super Sensitive Eddy-Current Electromagnetic Probe" and is incorporated herein by reference. This patent describes devices and methods for improved inspections of conducting structures of different shapes. An eddy-current probe includes an excitation coil unit, a magnetic detector within the probe, a signal-conditioning/preamplifier circuit within the probe, and a signal channel. The excitation coil unit is shielded on substantially all sides except an emission face that transmits an alternating magnetic signal to a conducting (e.g., metal) object, such that the metal object modifies the alternating magnetic signal. The magnetic detector within the probe is also shielded on substantially all sides except a reception face, such that the alternating magnetic signal as modified by the metal object is received into the shielded magnetic detector and converted into a first electrical signal. The signal-conditioning/preamplifier circuit within the probe is shielded on substantially all sides, and provided with electrical power. The shielded preamplifier provides detection for very small signals, such as from magnetic probing of aircraft-skin metals. Other embodiments include a traveling-wave excitation structure and a multiple-phase driving circuit, some of which include the shielded pre-amplifier, and others of which are not shielded. An eddy scope is described that provides a multiple-phase excitation signal to various different probes.

U.S. patent application Ser. No. 11/114,507 (now U.S. Pat. No. 7,301,335) filed by Yushi Sun and Tianhe OUYANG on Apr. 25, 2005, is titled "APPARATUS AND METHOD FOR RFEC SCANNING A SURFACE TO DETECT SUB-SURFACE CRACKS AROUND RIVETS AND THE LIKE" and is incorporated herein by reference. This patent Application describes an RFEC excitation unit and sensor apparatus and method that facilitate detection of cracks or other anomalies within or under a surface and immediately next to an expected structure (such as a rivet) that would otherwise cause a signal change and prevent detection of the cracks or other anomalies. In some embodiments, the apparatus includes actuators and control mechanisms that move the apparatus and analyze sensed RFEC signals to determine the location of the rivet, and then to rotate (mechanically or electronically) the sensed signal and/or excitation signal to maintain a constant relationship to the edge of the rivet in order that signals from the rivet edge are suppressed and signals from the cracks or anomalies are detected. In some embodiments, the excitation unit is maintained at the center of the rivet surface, and the sensor is moved around the rivet in a circle centered on the rivet.

FIG. 15 is a schematic block diagram of the excitation driver and sensing demodulator 1500 of apparatus 100. In some embodiments, eddy-current detection-and-display system 101 includes a sine-wave and cosine-wave generator 1520 that outputs sine and cosine versions of a wave having a selected frequency useful for scanning the object 99 (e.g., selected for the type of metal and its configuration and thickness). In some embodiments, the cosine($\omega$t) signal 1521 is buffered through adjustable amplifier 1523 having an amplification factor A, and the resulting signal A*cosine($\omega$t) is connected through an impedance (such as the resistance 1540 shown, or another suitable impedance such as one including resistance, capacitance, and/or inductance) to a selected coil 129 through analog switch 122 and/or mux 121, and the selected coil 129 is also connected to one input of differential amplifier 1528. In some embodiments, the cosine($\omega$t) signal is also buffered through adjustable amplifier 1524 having an amplification factor B, and the resulting signal B*cosine($\omega$t) is connected through an impedance (such as the resistance 1541 shown, or another suitable impedance such as one including resistance, capacitance, and/or inductance) to a selected reference coil 125 through analog switch 122 (and/or a mux, not shown), and the reference coil 125 is also connected to one input of differential amplifier 1528. The differential amplifier outputs a difference signal that represents the difference between the selected sense coil 129 and the selected reference coil 125 (e.g., difference signal 1593=$E^*\text{cosine}(\omega + \alpha)$). The difference signal is mixed (i.e., multiplied) by demodulator 1525 with the $\text{cosine}(\omega t)$ signal 1521 (e.g., in some embodiments, with resulting after demodulation signal Xm 1594=$\text{cosine}(\omega t)^*(E^*\text{cosine}(\omega+\alpha))=\frac{1}{2} E^*(\text{cosine}(2\omega+\alpha)+\text{cosine }\alpha)$, then goes through low-pass filter 1526 (e.g., in some embodiments, with resulting after low-pass filter signal Xp 1596=$K^*\text{cosine}(\alpha)$, where, in some embodiments $K=\frac{1}{2} E$) and H gain amplifier 1527 (e.g., in some embodiments, with resulting after horizontal gain amplifier signal X 1598=$Kh^*Xp$ (where Kh is the horizontal gain)), and represents the real component of a signal having real and imaginary components based on the phase and amplitude changes of the selected sense coil 129. The difference signal is also mixed (i.e., multiplied) by demodulator 1535 with the $\text{sine}(\omega t)$ signal 1522 (e.g., in some embodiments, with resulting after demodulation signal Ym 1595=$\text{sine}(\omega t)^*(E^*\text{cosine}(\omega+\alpha))=\frac{1}{2} \; E^*(\text{sine}(2\omega+\alpha)+\text{sine}(\alpha))$, then goes through low-pass filter 1536 (e.g., in some embodiments, with resulting after low-pass filter signal Yp 1597=$K^*\text{sine}(\alpha)$, where, in some embodiments, $K=\frac{1}{2} E$) and V gain amplifier 1537 (e.g., in some embodiments, with resulting after vertical gain amplifier signal Y 1599=$Kv^*Yp$ (where Kv is the vertical gain)), and represents the imaginary component of a signal having real and imaginary components based on the phase and amplitude changes of the selected sense coil 129. These two signals are then processed by rotator 1538 which has input factors cosine(beta) and sine(beta) that are used to rotate the signals by an angle (beta), which are then output as real component 1533 and imaginary component 1534.

SUMMARY OF THE INVENTION

In some embodiments, the invention provides an apparatus that includes a plurality of coils (e.g., numerous thin-film coils formed in an array on a flex circuit), each of the coils acting as an excitation unit that generates an alternating excitation magnetic signal; and as a sensor that is configured to detect eddy-current-signal phase and amplitude changes (due to anomalies in the surface being inspected) relative to the excitation magnetic signal. In some embodiments, the apparatus is configured to electronically scan a surface (e.g., of a metal plate) by successively switching to individual ones of the plurality of excitation/sensing coils (using, e.g., an analog multiplexer or switch) without physical movement of the apparatus in order to detect anomalous signal changes in a manner that reduces signal changes due to probe lift-off between the probe and the surface.

In some embodiments, each coil is connected one at a time to an excitation signal (e.g., through a resistance), and the phase and amplitude changes due, for example, to a crack or other defect in the surface, are used to identify the position of the crack. In some embodiments, a reference coil (in some embodiments, a selected one of a plurality of different reference coils or reference coils placed against different reference substrates) is selectively connected as one input to a differential amplifier, and a selected one of the plurality of excitation/sensing coils is selectively connected as the other input to the differential amplifier. In some embodiments, the selected reference coil and the selected sensing coil are each driven with a selected amplitude of an AC excitation signal having a frequency suitable for detecting anomalies in the surface being inspected. The output of the differential amplifier is then fed to each of two demodulators (e.g., analog multipliers or mixers), and is "demodulated" in the first demodulator by multiplication by a cosine version of the excitation signal followed by a low-pass filter (LPF) and an "H-gain" amplifier (with a gain factor of "H") to obtain a first (H) demodulated signal, and is "demodulated" in the second demodulator by multiplication by a sine version of the excitation signal followed by a low-pass filter (LPF) and a "V-gain" amplifier (with a gain factor of "V") to obtain a second (V) demodulated signal. In some embodiments, the resulting first and second demodulated signals are then linearly combined using parameters (e.g., cosine(beta) and sine(beta)) to obtain the real and imaginary portions of the sensed signal.

In some embodiments, a calibration step is performed (using either the sensing coils on a calibration sheet or piece of metal, or a dedicated calibration coil on a calibration piece of metal), in order to characterize what the real and imaginary portions of the sensed signal look like when various types and depths of defects are present and when no defect is present. In some embodiments, the metal sheet used for the calibration step is of the same metal composition(s) and thickness(es) as the metal of the object (such as an aircraft wing or turbine blade) that will be sensed. In some embodiments, the calibration data are stored in a computer and then used to compare against the sensed signals from the coil array.

In some embodiments, the invention provides an apparatus that includes a plurality of excitation/sensing coils, a reference coil, an excitation-signal generator having a first buffered output, a second buffered output, a cosine output and a sine output, a differential amplifier having a first input operatively coupled to the first buffered output and a second input operatively coupled to the second buffered output, a first analog multiplexer (mux) that selectively couples one of the plurality of excitation/sensing coils to the first input of the differential amplifier, and wherein the reference coil is operatively coupled to the second input, and wherein a sensed-signal output of the differential amplifier is demodulated using the cosine output and a sine output of the excitation-signal generator to obtain real and imaginary components of the sensed-signal output.

Conventional eddy-current systems can be configured in different modes, such as absolute mode, differential mode, reflection (or drive/pickup) mode, etc. In some embodiments, there is only one coil/unit used in absolute mode; while two coils are used in differential mode (e.g., a reference coil signal is subtracted from the excitation/sensing coil signal), but each of the two coils works as the excitation (drive) and sensing (pickup) at the same time. In some embodiments, separated drive and pickup coils/units are used in the reflection mode.

In some embodiments, the working principle of a magnetic carpet probe (MCP) according to the present invention is the same as for a conventional eddy-current probe working in differential mode. In some embodiments of the present invention, one coil is used to electromagnetically sense the object and the other coil acts as a reference to which to compare the sensed signal. In some embodiments, the differences between the present invention and a conventional eddy-current probe include: (a.) the two-dimensional (2D)—coil array of the test unit that allows a quick and static electronic scan (i.e., a scan done without moving the sensor array relative to the section of the object being scanned), which eliminates mechanical "noise" (signal changes due to variations in distance between the coils and the object being sensed); (b.) coils are formed in a piece of flex circuit that can conform to a surface of complex geometry; and (c.) there is substantial flexibility in controlling parameters of the scan and data display using a programmable device.

BRIEF DESCRIPTION OF THE DRAWINGS

The patent or application file contains at least one drawing executed in color. Copies of this patent or patent application publication with color drawing(s) will be provided by the Office upon request and payment of the necessary fee.

FIG. 3 is a block diagram of a MCP system 300 of a typical magnetic carpet probe 100 according to some embodiments of the invention.

DETAILED DESCRIPTION OF THE INVENTION

Figure 1:
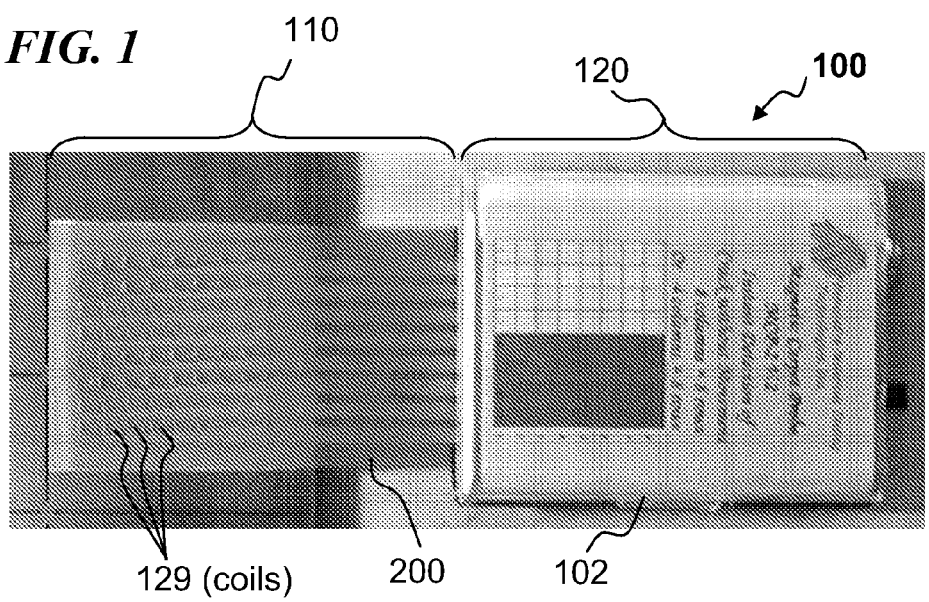
FIG. 1 is a photograph of a typical magnetic carpet probe (MCP) 100 according to some embodiments of the invention.

In the following detailed description of the preferred embodiments, reference is made to the accompanying drawings that form a part hereof, and in which are shown by way of illustration specific embodiments in which the invention may be practiced. It is to be understood that other embodiments may be utilized and structural changes may be made without departing from the scope of the present invention.

The invention provides methods and apparatuses that can be used to scan an object for an anomaly. Generally, an apparatus of the invention is placed onto a surface of the object to be scanned so that an excitation-sensing unit that is a part of the apparatus is positioned to force an alternating excitation magnetic field into the object. The magnetic field produces conventional eddy currents that can be detected in close proximity to the excitation unit.

The amplitude and phase of the eddy-current of an excitation-sensing coil will stay substantially equal to the amplitude and phase of the eddy-current of a reference coil if both are placed against substantially similar thicknesses and substantially similar compositions of metal or other conductive materials. However, anomalies that are in the material making up the object being scanned and that are not in the material against the reference coil (i.e., defects that cause the magnetic-transmission characteristics of the material being scanned to change at the point of the anomaly) will cause the relative phases and amplitudes to differ between the reference coil and excitation/sensing coil. Accordingly, anomalies can be detected by determining if the magnetic-transmission characteristics of the material being scanned are consistent with the presence or absence of an anomaly.

Through use of the methods and apparatuses of the invention, anomalies that are exposed on a surface can be detected. Anomalies that are present below the surface of a layer of material making up the object being scanned can also be detected. For example, a sheet or plate of material, such as metal, can be scanned to determine if there are anomalies within the sheet of metal. Examples of such anomalies include differences in composition of the material being scanned that are caused by contaminants such as minerals, other metals, changes in the percentages of metals in an alloy, and the like. Anomalies can also be detected that are due to physical differences in the material being scanned such as cracks, bubbles, fissures, cavities, and the like.

In some embodiments, the method and apparatus of the invention are used to scan a multilayered and/or laminated object in order that anomalies located on the surface of the object can be detected. In some embodiments, anomalies that are present slightly below the surface of a layer of material making up the object being scanned can also be detected.

Magnetic-Carpet-Probe Technology for Engine Inspection

Anomalies in aircraft engine components may be initiated during its operation or may result from manufacturing event lapses. Surface anomalies are seen most often, but anomalies also can occur deep within engine materials. Undetected anomalies can result in catastrophic failure of the component. Current NDE (non-destructive evaluation) techniques such as fluorescent penetrant inspection (FPI) and etching processes rely on visual line-of-sight inspections to detect these anomalies. These techniques are often inadequate due to geometry of parts being inspected, and are not quantifiable by conventional Probability of Detection (POD) statistical methods.

An eddy-current pencil probe can detect small surface cracks and other anomalies. However, the scan process is very slow and difficult to apply to curved surfaces. Manual scan can cause operator fatigue and the inspection quality is largely dependent on the skill and work attitude of an operator. The few emerging techniques for large-area surface/subsurface inspection are still in their research stages. Examples include Meandering Wire Magnetometer (MWM), Eddy Current (EC) Array Probe, Ultrasonic (UT) Array Probe, Guided UT Probe, etc. However, they have a few common shortcomings, such as:

A. In all of these methods, it is essential to mechanically move a probe over the surface under inspection. Such movement causes significant noise and limits the sensitivity of flaw detection.

B. Many of these methods have directionality problems. In other words, they lack sensitivity for cracks/flaws in a certain direction.

C. They have little potential to be extended for detection of flaws deeply hidden in the materials of an engine component because of skin-depth effect or other restrictions of their signal penetration.

More advanced non-destructive inspection (NDI) techniques are needed to increase the safety and decrease the failure of aircraft engines.

Magnetic Carpet Probe

Figure 2A:
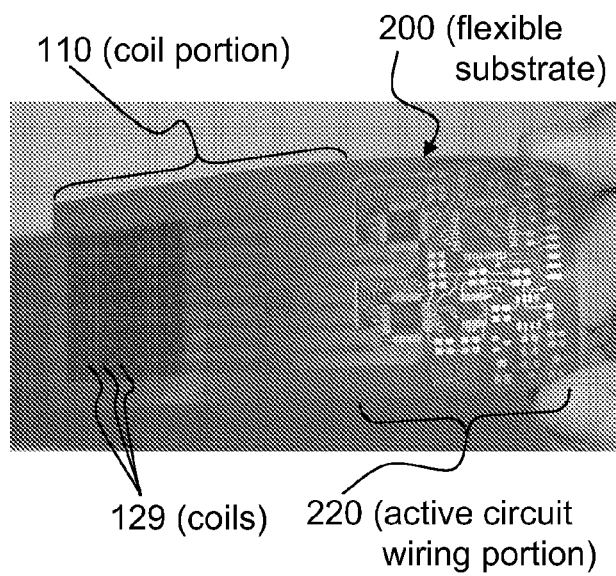
FIG. 2A is a photograph of a typical magnetic-carpet-probe substrate 200 according to some embodiments of the invention.

FIG. 1 is a photograph of a typical magnetic carpet probe (MCP) 100 according to some embodiments of the invention. In some embodiments, MCP 100 includes a flexible circuit substrate 200 having a plurality of coils 129 located on a coil portion 110, and an enclosed circuitry portion 220 (See FIG. 2A) that is populated with surface-mount integrated circuits and other active and/or passive components to form probe-control unit 120, and is packaged in enclosure 102. In some embodiments, enclosure 102 is soft and flexible to enhance the overall maneuverability of MCP 100, FIG. 2A is a plan-view photograph of a typical flex-circuit magnetic-carpet-probe substrate 200 according to some embodiments of the invention. In some embodiments, MCP substrate 200 includes a plurality of coils 129 located on a coil portion 110, and a circuitry-mounting portion 220 (the wiring and solder tabs for connecting surface-mount integrated circuits and other active and/or passive components (not shown here)).

Figure 2B:
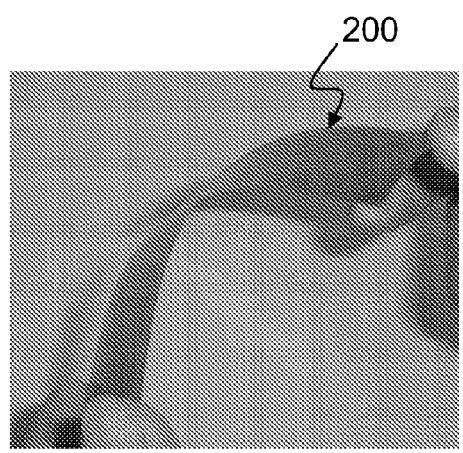
FIG. 2B is a photograph of a magnetic-carpet-probe substrate 200 according to some embodiments of the invention.

FIG. 2B is a side-view photograph of the MCP substrate 200 shown in FIG. 1 and FIG. 2A, according to some embodiments of the invention.

FIG. 3 is a block diagram of a typical MCP system 300 that uses magnetic carpet probe 100 according to some embodiments of the invention. In some embodiments, system 300 includes an MCP 100 and a portable super-sensitive eddy-current (SSEC) system 330. In some embodiments, SSEC 330 includes, or is implemented in, a laptop personal computer (e.g., an IBM-PC® compatible or Apple® PowerBook® compatible laptop) having an interface-circuit card (see FIG. 15 below) connected to a cable 133 and plug 132 that interfaces into socket 131 on the MCP 100 (a block-diagram schematic of the circuitry of MCP 100 is shown within the dotted lines). In operation, MCP 100 is placed against a surface of the object under inspection (OUI) 99. In some embodiments, a plurality of coils 129 arranged in a two-dimensional (2D) array are located on a coil portion 110 of a flex substrate 200, and MCP-probe circuitry 120 is mounted on and electrically connected by circuitry-mounting portion 220 (the wiring and solder tabs for connecting the electronics that include surface-mount integrated circuits and other active and/or passive components shown in block-diagram fashion here). In some embodiments, the coils 129 are connected to multiplexer (mux) 121 (which includes one or more muxes, as described below regarding FIG. 16) which selects one or more of the coils to be connected at successive times to SSEC 330, optionally using a gain circuit 124. Controller 123 (in some embodiments, a programmable-logic control chip) is used to control mux 121 which determines which coil 129 is connected at which times. In some embodiments, one or more reference and/or calibration coils 127 are also connected through mux 121. This allows the MCP 100 to operate in differential mode (where one of the reference coils 127 and one of the probe coils 129 are simultaneously connected in a differential connection to SSEC 330) in order to observe the differential response of these coils. This also allows the MCP 100 to be calibrated (where one of the calibration coils 127 and one of the reference coils 127 or probe coils 129 are simultaneously or sequentially connected to SSEC 330) in order to obtain calibration data for each coil based on a comparison of the responses of these coils. In some embodiments, the calibration data is stored and later used to adjust the received signals obtained to get better results or displays of the data. See FIG. 14 and FIG. 15 below for further descriptions of a similar system.

A Magnetic Carpet Probe (MCP) technique is included in some embodiments for rapid large-area inspection for the detection of tiny cracks and other anomalies in flat and curved surfaces of conductive (e.g., aluminum) and less-conductive (e.g., titanium) metallic components. In some embodiments, the present invention includes four major components:

a. A thin (~few mils, or a few times 0.0254 mm) flexible printed-circuit board ("FPCB" or "flex substrate" 200—see FIG. 2).

b. Circuitry and coils to generate a traveling magnetic wave to scan the inspected area.

c. A soft and flexible cover.

d. Data-Acquisition System Built Into a Portable Super-Sensitive Eddy-Current ("SSEC") System 330—see FIG. 3.

The idea of applying a traveling magnetic wave in nondestructive inspection is described in U.S. Pat. No. 6,636,037 issued to Tianhe OUYANG on Oct. 21, 2003, titled "Super Sensitive Eddy-Current Electromagnetic Probe", and in U.S. patent application Ser. No. 11/114,507 (now U.S. Pat. No. 7,301,335) filed by Yushi Sun and Tianhe OUYANG on Apr. 25, 2005, titled "APPARATUS AND METHOD FOR RFEC SCANNING A SURFACE TO DETECT SUB-SURFACE CRACKS AROUND RIVETS AND THE LIKE", which are incorporated herein by reference.

Flexible Printed-Circuit Board (FPCB) 200.

Figure 14:
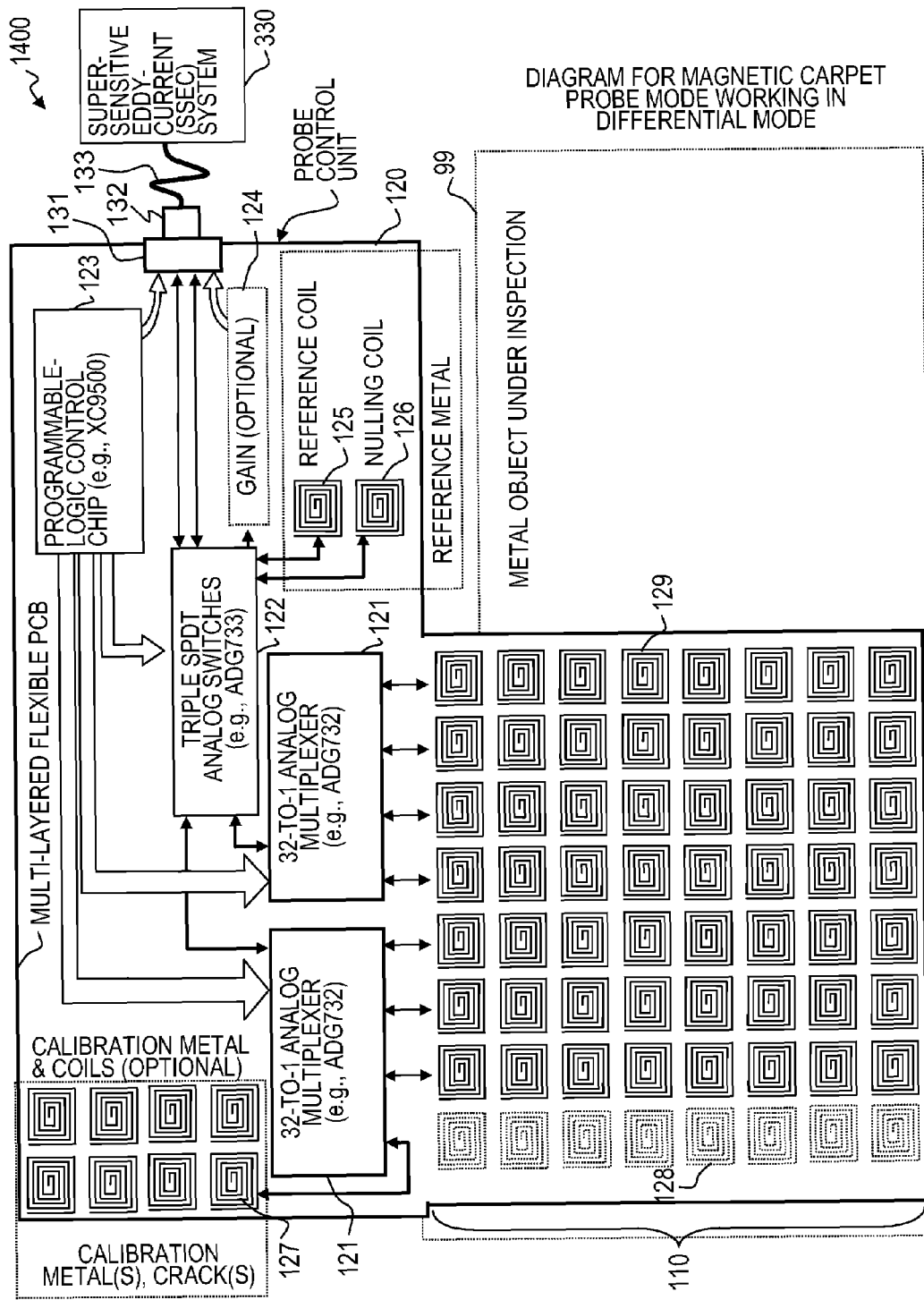
FIG. 14 is a schematic block diagram of an apparatus 1400 having a sensor that includes a plurality of excitation/sensing coils that are electronically scanned to determine a position of a defect in a surface of an object.

In some embodiments, the sensor portion of an MCP is made of a piece of thin flexible PCB 200 as shown in FIG. 2, with densely populated printed coil sensors on it, such as, for example, coils 129 shown in FIG. 14.

The major advantages of using a flexible PCB 200 include:
a. It is light weight;
b. It is easy to conform to a curved surface due to its extremely thin and flexible structure; and
c. It has significantly lower cost due to the modern and highly efficient technology in PCB fabrication.

Flexible PCB technology has been stepping forward quickly in recent years. This has made it possible to build thin, tiny and multiple-turn coils on such a board. Currently, the limits for the width and spacing for a printed wire is about 0.002". This makes it possible to build, say, a six-turn (6-turn) PCB coil within a 0.040" by 0.040" (i.e., 1.016 mm by 1.016 mm) or 0.060" by 0.060" (i.e., 1.524 mm by 1.524 mm) area and meet the fundamental NDI requirements in signal resolution. A thin-layer conducting material may shield the coils very well because of the extremely close distance between a shield and the shielded object built in the same flexible printed-circuit board (FPCB 200).

Because of its extremely small thickness, an FPCB 200 can be placed, pasted (e.g., affixed with adhesive), or deposited as films (e.g., one or more layers of insulating material such as silicon oxides or polymer films alternated with conductive films (such as copper or other suitable metal or other conductor deposited using shadow masks or as a solid layer that is etched using photolithography to define the conductor paths and coils). This is done easily on a flat or slightly curved surface of a critical area of an aviation component, such a piece of an aircraft-engine propeller, a surface of an engine disc web or bore. The coil sensors can directly sense the surface of the material in the areas covered by the sensors. Because an FPCB is placed or affixed ("pasted") on top of the surface under inspection, the sensors have closest and fixed spacing from the inspected surface, resulting in the highest possible sensitivity to surface conditions. In some embodiments, the MCP probe 100 is built as part of, or laminated to, the structure being inspected and left in place permanently. Furthermore, noise due to mechanical movement of a probe, present in other NDI techniques, is completely eliminated.

Figure 12:
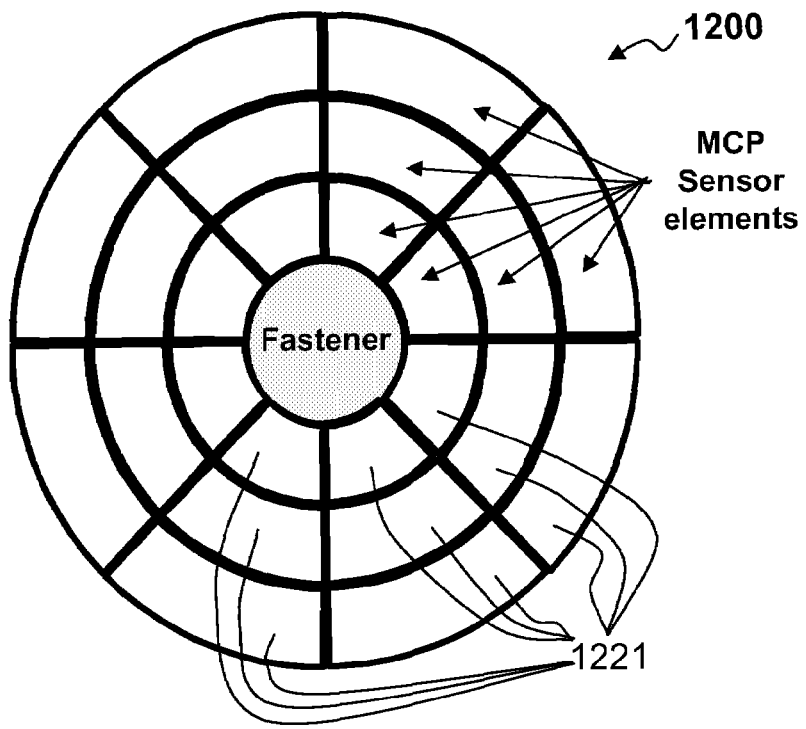
FIG. 12 is a block diagram of a radial layout 1200 of an MCP for structural monitoring and crack detection near a hole with a fastener.
Figure 13:
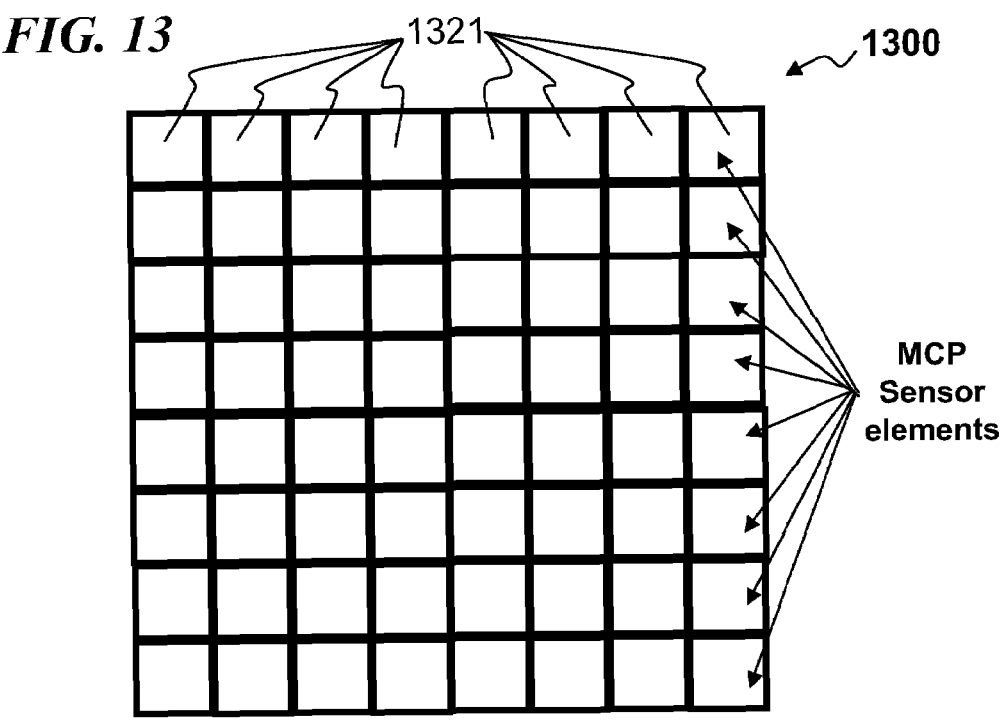
FIG. 13 is a block diagram of a rectilinear layout 1300 of an MCP for structural monitoring and crack detection of an area without a fastener.

Two possible Magnetic Carpet Probe (MCP) sensor embodiments are described here. Embodiment A (such as an MCP configuration 1300 having a regularly spaced array in two dimensions such as shown in FIG. 13) is for inspecting an area where there are no obstacles; Embodiment B (such as an MCP configuration 1200 having coils placed around a circumference of an object such as rivet or axle, such as shown in FIG. 12, or coils otherwise regularly spaced along a regular or irregular boundary) is for inspecting an area around hole, such as impeller bore holes, where the signal measured by the sensors may be influenced by the edge of the hole.

Using a Traveling Magnetic Wave to Scan the Inspected Area

In some embodiments, multiple-phase AC currents are applied to the MCP sensor PCB (for further details, see U.S. Pat. No. 6,636,037 and U.S. patent application Ser. No. 11/114,507 (now U.S. Pat. No. 7,301,335), which are described above, and incorporated herein by reference) to generate a traveling magnetic wave, i.e., an electronically controlled moving magnetic field, on top of the to-be-tested surface (e.g., an aircraft-component surface) without physically moving the MCP 100. The operation of a traveling magnetic wave is, in some embodiments, identical to a physical movement of a piece of permanent magnet with a pair of N and S poles. This time-varying field generates induced current in the conducting material of an aircraft component. The interaction of the induced current with a crack generates a vertical magnetic field that is sensed by coil sensors of the MCP.

The major advantages of using traveling-magnetic-wave MCP excitation include:

a. Traveling-wave excitation generates a magnetic field stronger than that of a conventional AC excitation seen, for example, in an MWM, EC array sensor, etc.
 b. Traveling-wave excitation may provide a uniform magnetic field over the entire covered area and enable use of two-dimensional sensor arrays. There are no two-dimensional mountable MWM arrays available today in the literature.
 c. Traveling-wave excitation may generate eddy currents with alternating direction at each point of an inspected component. Therefore, an MCP has sensitivity to a crack of any orientation, while the UT guided wave (UTGW) or mountable MWM techniques both have directionality problems, in other words, they lack sensitivity to cracks of a certain orientation.
 d. The possibility of expanding the MCP technique to include a flat-geometry remote-field eddy-current (FG RFEC) technique for detecting flaws deeply hidden in materials of an aircraft component or other inspected object.

The aging United States Air Force aircraft fleet and increasing complexity of mission requirements have created a need for nondestructive inspection having both increased range and complexity to provide continuing assurance of aircraft structural integrity. The challenge of increased needs and stringent requirements is coincident with decreasing budgets and mission-response demands. These challenges must be met by increasing efficiencies in both nondestructive inspection (NDI) coverage and anomaly-detection-and-analysis capabilities. New NDI tools, procedures and life-cycle management protocols are required to meet these challenges and to provide continuing confidence in aircraft structural/mission integrity at all flight-line and maintenance levels. New tools and management protocols include the use of embedded sensors (health monitoring), more rapid/broad-area coverage of structural components, and increased reliability of all inspection operations. Methods to provide more frequent, reliable monitoring of critical components and structures areas without (or with minimal) disassembly are required to meet near-term and future aircraft structural-integrity challenges—at significantly reduced manpower and maintenance-operations costs.

The inherent NDI challenges in complex modern aircraft include:

a. Difficulty in accessing high-stress areas prone to cracking;
 b. Thick (accessible) outer skins with requirements to assess the integrity of underlying structures.
 c. Complex geometries which can complicate the inspection process, with geometrical variations generating signals that may be comparable or even much greater than a crack signal obtained from an accessible inspection site.
 d. Inhomogeneous multi-layer structures which can alter crack signals.

New NDI challenges therefore include not only include requirements for new NDI methods and procedures, but also new methods to address increasingly complex assemblies at reduced cost.

Aircraft-maintenance cost is also a critical issue. Inspection costs consist primarily of aircraft transportation, parking, and disassembly to facilitate inspection; the inspection itself comprises only a small percentage of the total cost. Currently, maintenance is scheduled by number of flight hours or flight cycles and actual aircraft usage. Maintenance cost can thus be significantly reduced to the extent that aircraft health can be reliably monitored on an ongoing basis, allowing flight-mission planning to proceed more smoothly because maintenance need only be performed when it is necessary. Aircraft structural integrity can be monitored by attaching small embedded sensors in critical, often inaccessible areas, with easily accessible outlet connections. An operator can then access these outlet connectors and check the aircraft's condition on a mission-usage basis, thus allowing ongoing monitoring of important aspects of aircraft health.

There are a number of requirements an embedded sensor has to meet to enable such an ongoing monitoring of aircraft structures. These include:

a. High reliability and data integrity;
 b. Robustness in a harsh working environment;
 c. Capability for in-situ verification and calibration;
 d. Thin and small configuration to be firmly attachable in the interior of an aircraft, yet conformable to complex aircraft geometries;
 e. Sufficiently high-speed operation to quickly scan large areas, yet flexible and powerful enough to provide detailed information about a range of structures;

f. Simple enough in use to enable rapid, routine data collection and interpretation by line and depot personnel;

g. Low cost and low power consumption; and h. Low cost and complexity of sensor replacement.

There are a number of embedded sensors in the development stage for aircraft-health-monitoring applications (i.e., applications that monitor the structural integrity of the aircraft itself), primarily based on two different physical approaches to detecting structural flaws: guided ultrasonic waves and eddy-current (electromagnetic) detection. Among these candidates for embedded sensors, the MAGNETIC CARPET PROBE (MCP) described here meets all the above requirements, as will be discussed below. A typical MCP device 100 is shown in FIG. 1.

Brief Description of a Magnetic Carpet Probe (MCP)

An MCP is a two-dimensional (2-D) eddy-current array built on a multi-layer flexible printed-circuit board (FPCB), more commonly referred to as a flex circuit. The overall thickness of such a flex circuit will typically range from 0.008" to 0.025", allowing it to be flexible enough to conform to the complex surfaces of an on aircraft, as illustrated in FIG. 2A and FIG. 2B.

A block diagram of the MCP is shown in FIG. 3. An electronic-scan (E-scan) program is written in a programmable chip, e.g., a Field Programmable Gate Array (FPGA) or Complex Programmable Logic Device (CPLD). This program controls the E-Scan sequence of applied AC current, through multiplexers, over the elements built in the 2-D array. The Super-Sensitive Eddy-Current (SSEC) system provides the AC current, processes the signals measured by each of the coil elements, identifies cracks above a predetermined threshold, and can simultaneously display a 2-D image of the scanned surface, a Crack Identification (Crack ID) image, highlighting signals of interest, and the crack signal value and crack location on the SSEC screen.

The programmable-logic control chip generates logic signals to perform scan operations, including:

a. Multiplexer timing signals for scanning the desired sequence of coils in the array;

b. Signals to operate the MCP in a calibration mode, to perform in-situ calibration;

c. Signals to operate the MCP in a differential mode, to increase sensitivity and reduce interference;

d. Signals to operate the MCP in a nulling mode, establishing a signal baseline from a user-selected null-point location on the screen.

e. Signals for E-scan area selection for special modes such as a zoom-in scan, etc.

Figure 4:
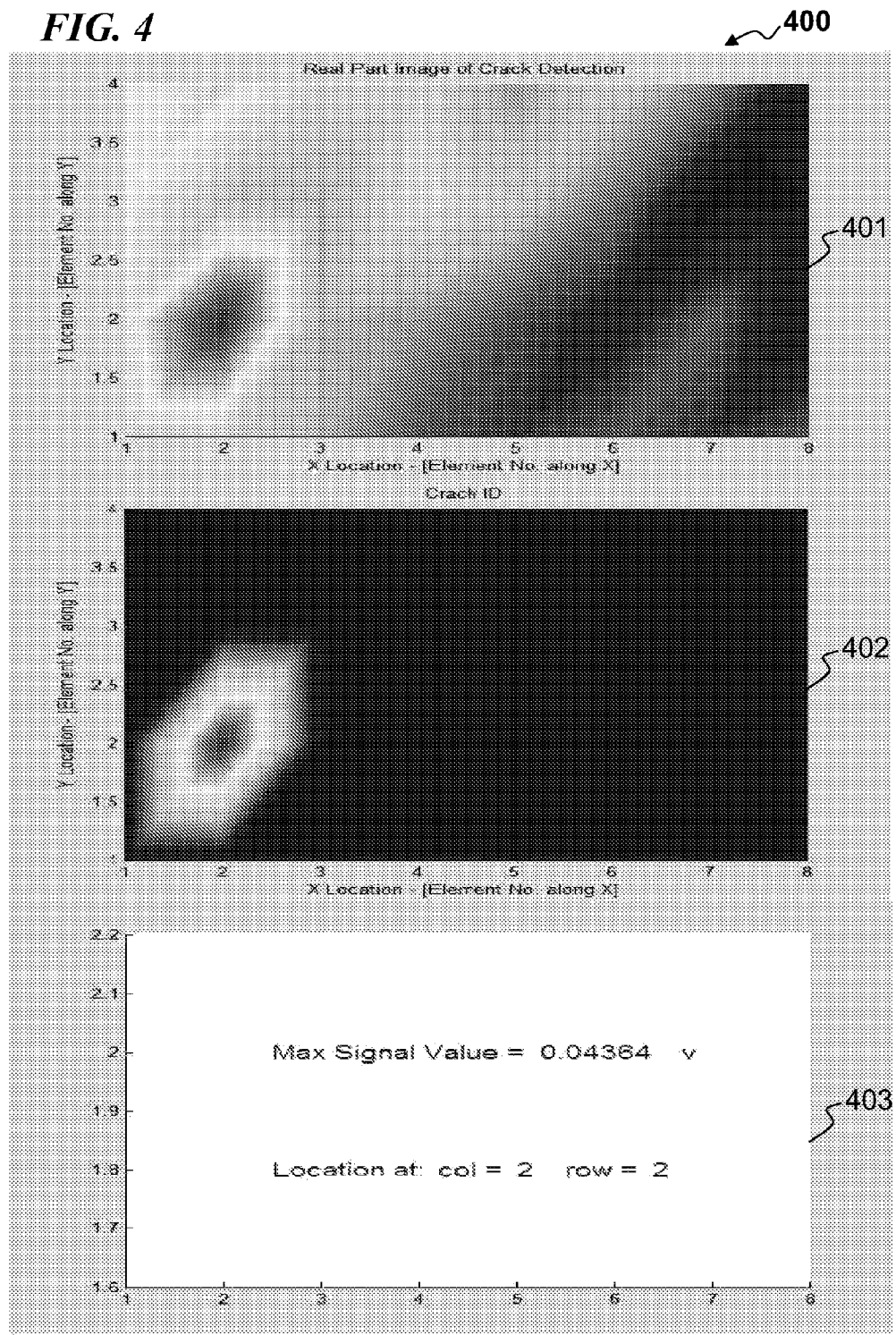
FIG. 4 is a screen-shot diagram 400 of three displays on one output monitor of the output of a MCP system 300 according to some embodiments of the invention.

FIG. 4 is a screen-shot diagram 400 that shows an example of this SSEC output for one embodiment of MCP 100. In some embodiments, screen-shot 400 includes three displays 401, 402, and 403 simultaneously on one output monitor (in other embodiments, these are displayed sequentially one after another) of the output of a Magnetic Carpet Probe 100. When no crack is found, the Crack ID window shows a uniform green color, and the information window reports "No Crack Found."

Figure 5:
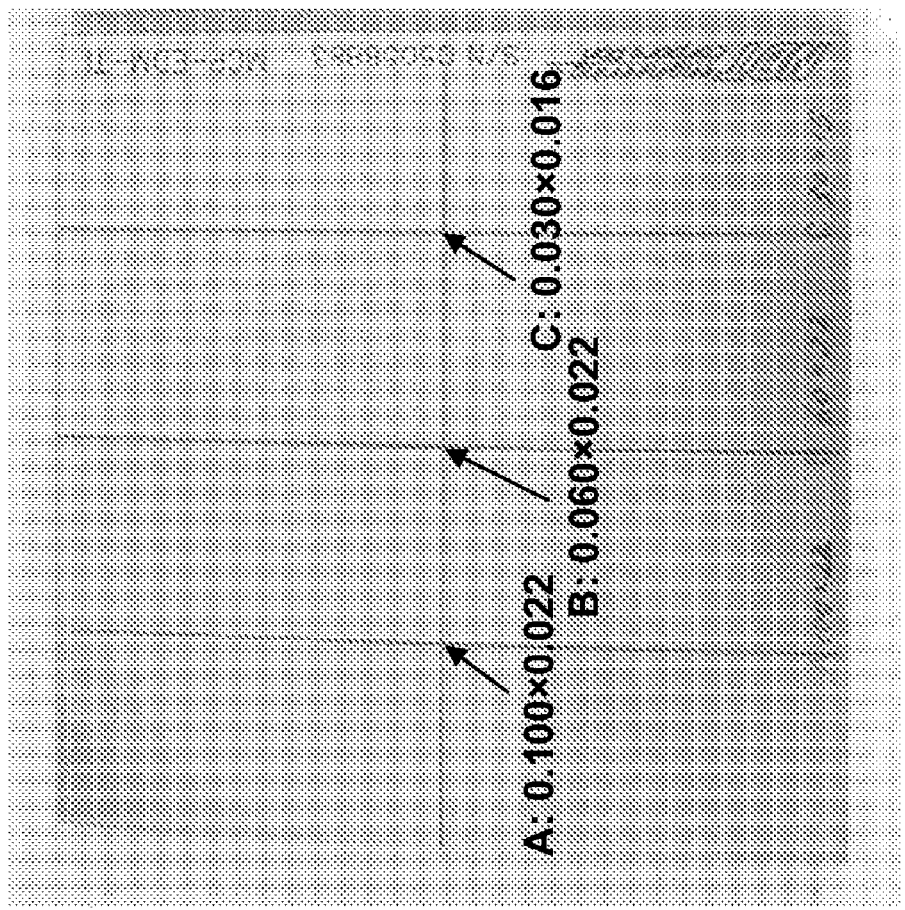
FIG. 5 is a photograph of a titanium standard 500 with Electrical-Discharge Machining (EDM) notches for use in testing a magnetic carpet probe 100 according to some embodiments of the invention.

FIG. 5 is a photograph of a titanium standard 500 (i.e., a plate made of titanium that has standard characteristics useful for testing and/or calibrating diagnostic equipment such as the present invention) with Electrical-Discharge Machining (EDM) notches for use in testing a magnetic carpet probe 100 according to some embodiments of the invention.

Figure 6:
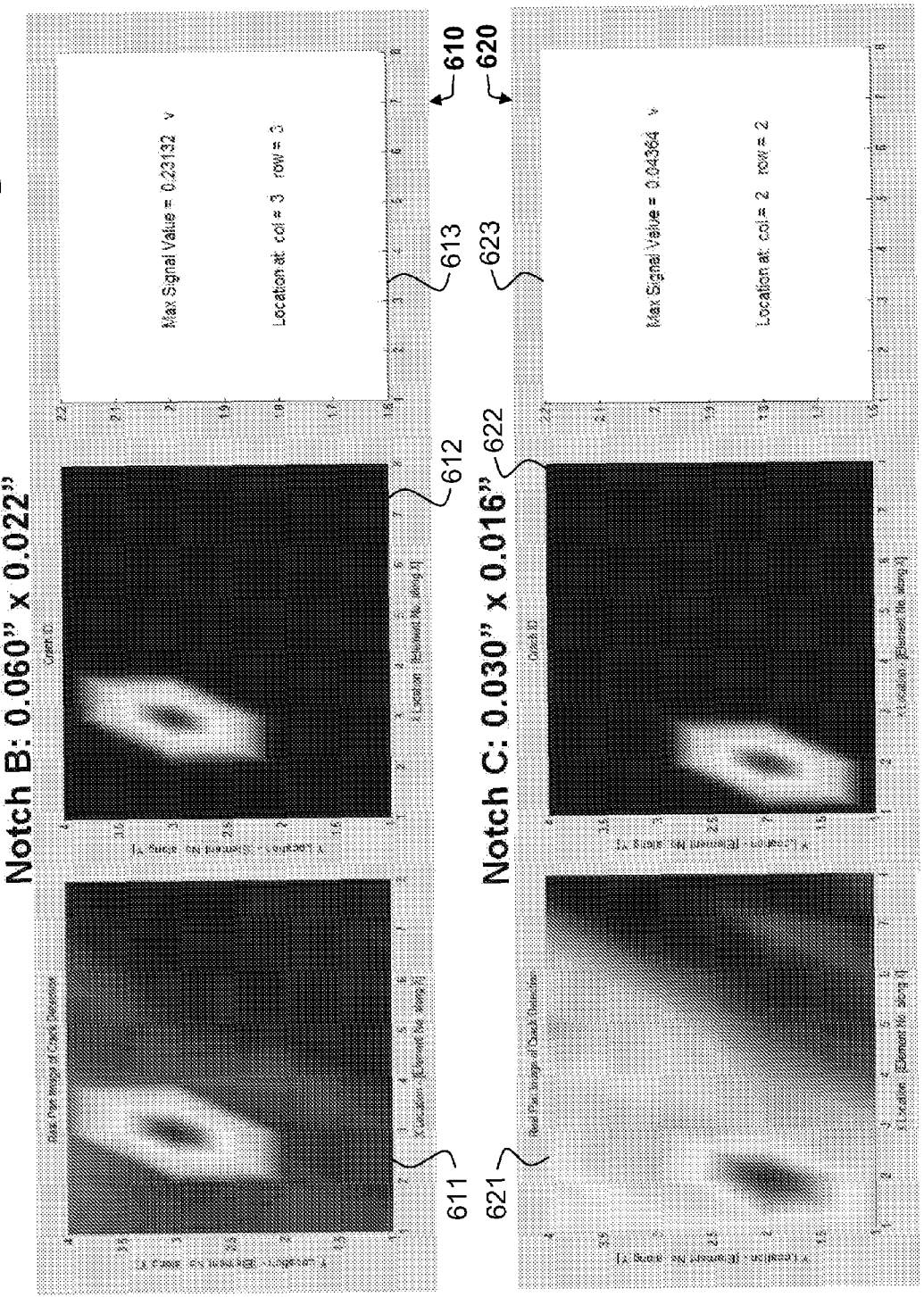
FIG. 6 is a diagram 600 of two screen-shots 610 and 620, each having a set of three displays of the output of a typical MCP system such as MCP system 300.

FIG. 6 is a diagram 600 of two screen-shots 610 and 620, each having a set of three displays of the output of a typical MCP system 300 according to some embodiments of the invention. In some embodiments, the upper screen shot (triple display 610) includes display 611 showing the image of a crack detection from a notch "B" having dimensions 0.060" by 0.022" (1.524 mm by 0.5588 mm)) correlating the crack to an X and Y location (e.g., (3,3)) of the coil(s) detecting the anomaly, display 612 showing an enhanced image of the crack detection (e.g., with background noise removed), and display 613 showing a textual description of the crack location and a crack characteristic (e.g., the maximum signal value, in some embodiments). In the lower screen shot, the triple display 620 includes display 621 showing the image of a different crack detection from a notch "C" having dimensions 0.030" by 0.016" (0.762 mm by 0.4064 mm)) correlating the crack to an X and Y location (e.g., (2,2)) of the coils detecting the anomaly, display 622 showing an enhanced image of the crack detection (e.g., with background noise removed), and display 623 showing a textual description of the crack location and a crack characteristic (e.g., the maximum signal value, in some embodiments).

Figure 7:
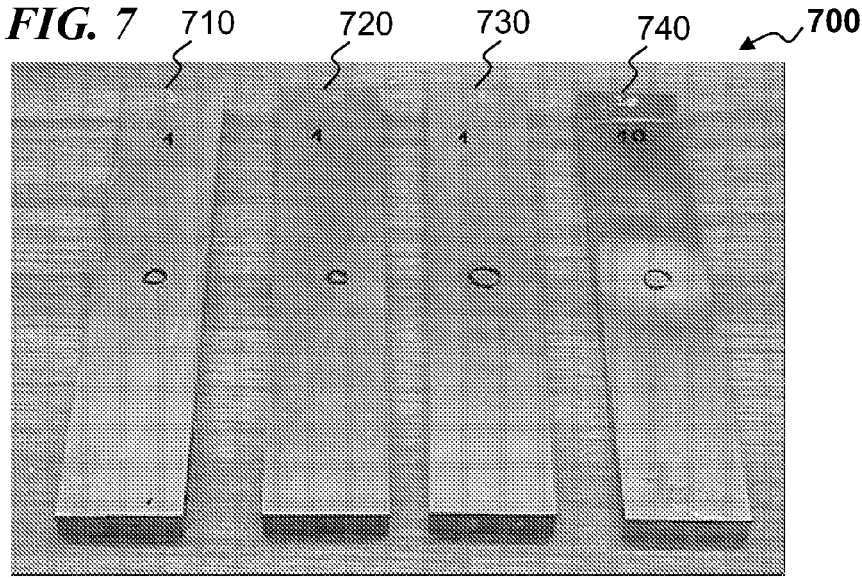
FIG. 7 is a photograph of four titanium specimens 700 with fatigue cracks.

FIG. 7 is a photograph of a set 700 of four titanium specimens 710, 720, 730, and 740, each having fatigue cracks having different characteristics. In some embodiments, MCP system 300 is calibrated and/or tested using such specimens that have well analyzed and understood anomalies.

Figure 8:
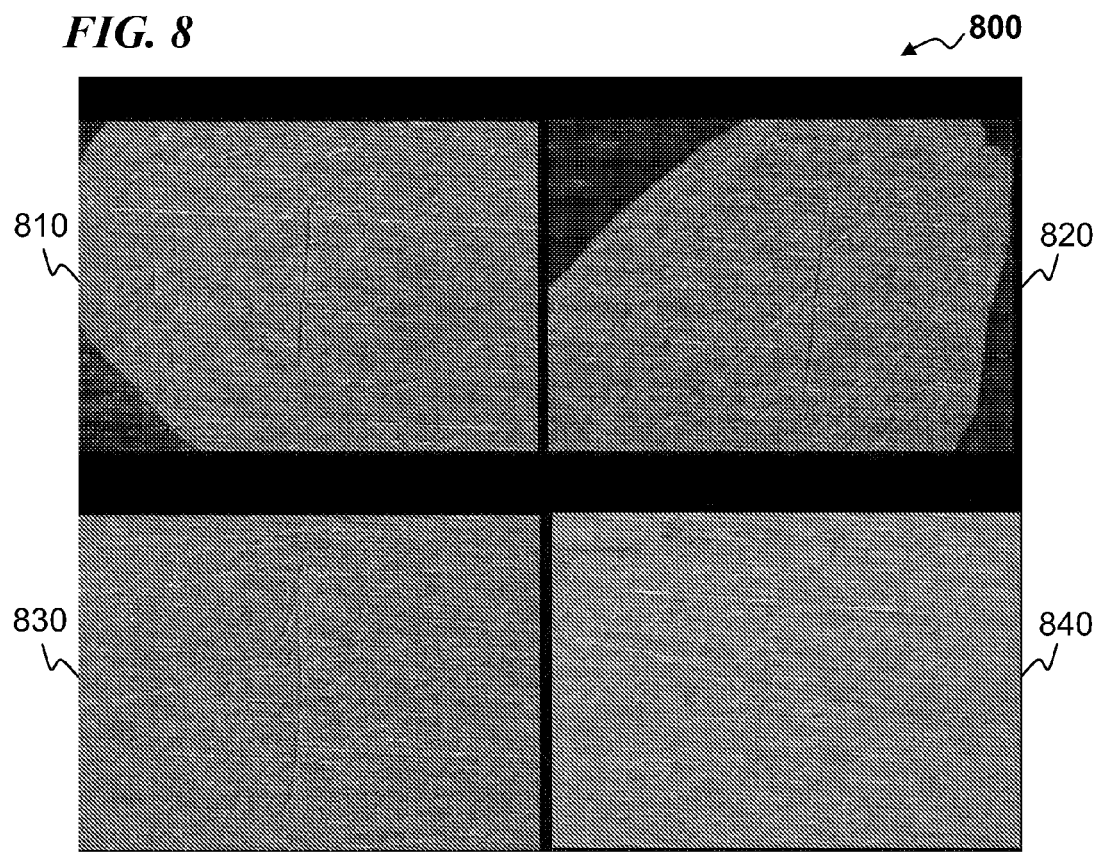
FIG. 8 is a photograph of microscope pictures of four fatigue-crack specimens 800.

FIG. 8 is a photograph of microscope pictures of a set 800 of four fatigue-crack specimens 810, 820, 830, and 840. In some embodiments, MCP system 300 is calibrated and/or tested using such specimens that have well analyzed and understood anomalies.

Figure 9:
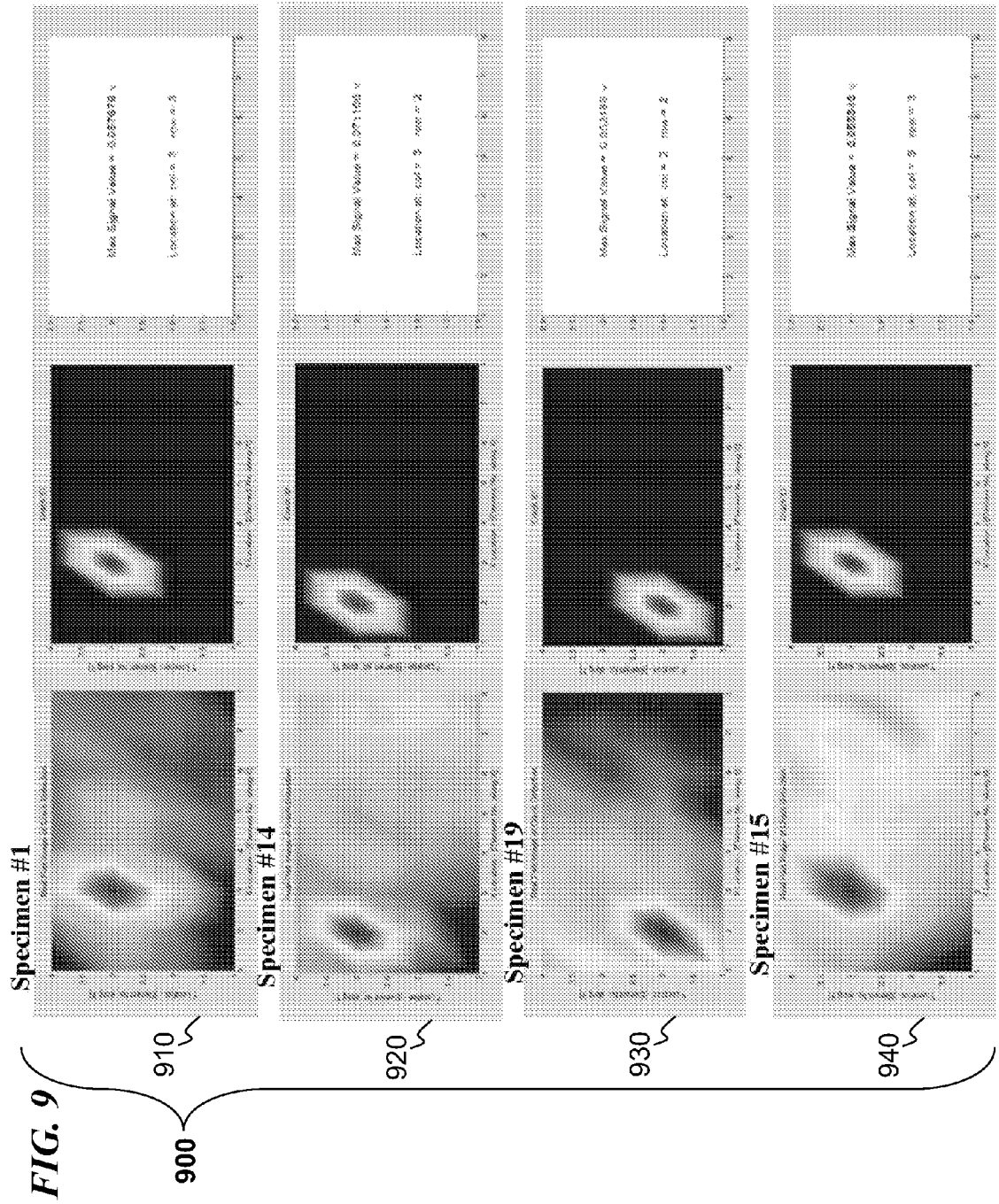
FIG. 9 is a diagram 900 of four sets of screen shots, each having three displays of the output of one embodiment of MCP system 300.

FIG. 9 is a diagram 900 of four sets of screen shots, each having three displays of the output of one embodiment of MCP system 300. Triple display 910 shows the analysis of a first specimen (#1), triple display 920 shows the analysis of a second specimen (#14), triple display 930 shows the analysis of a third specimen (#19)), triple display 940 shows the analysis of a fourth specimen (#15).

The unique advantages of the MCP compared with other approaches for crack detection include:

a. Completely static inspection: the probe need not move, since the electronic circuitry controls the location and timing of the magnetic field 1) No mechanical noise, ensuring high sensitivity; and 2) Electronically controlled magnetic scan—ensuring high-speed inspection of large areas.

b. A pure electronic device, with no mechanical parts or components:

1) Simplicity, robustness, light weight and reliability;

2) Ease in use; and

3) Low cost and low power consumption.

c. Based on a thin and flexible 2-Dimensional sensor array, some embodiments of the present invention provide the capability to:

1) Conform to a curved surface; and

2) Be attached to inaccessible or difficult-to-access areas for ongoing monitoring, d. Software-controlled call/reject action:

1) Minimum human factor involved; and

2) Possibility for future remote control of NDI and health monitoring through networking and/or wireless techniques.

A. The Magnetic Carpet Probe has Demonstrated Capability for High-Speed Inspection and Crack Detection.

The present invention has a demonstrated capability for high-speed inspection and crack detection. In some embodiments, it takes less then four seconds to scan a 1.4"×1.4" area and detect any cracks, including gathering and processing data and displaying the overall image of the scanned area, the Crack ID picture and information regarding crack signal value and crack location.

The test process on the some embodiments of the magnetic carpet probe includes the following steps:
  a. Firmly placing the MCP on a no-crack area;
  b. Clicking the A-Scan Button to start a scan and waiting a couple of seconds;
  c. Clicking Data Collection Button No. 1. No-crack data are collected and processed almost immediately;
  d. Firmly placing the MCP on an area of inspection and waiting a couple of seconds;
  e. Clicking Data Collection Button No. 2. Crack data are collected and processed, again almost immediately;
  f. Calling signal display code 'Demo_MCP1'. All three images appear on the screen in a couple of seconds;
  g. Repeating steps d., e., and f. for detecting cracks in other areas to be inspected.

Note that the bulk of the total time used for crack detection is spent in positioning the MCP on the areas to be inspected.

B. The Magnetic Carpet Probe has Demonstrated Capability High Sensitivity
  a. The MCP has demonstrated the ability to detect all of the Electrical-Discharge Machining (EDM) test notches on the titanium standard shown in FIG. 5. The minimum notch size is here 0.030"×0.016".
  b. All of real cracks on titanium Specimens #1, #14, #15 and #19, as shown in the displays shown in FIG. 6, were detected. Their lengths were between 0.024" and 0.036".

Note that titanium materials have very low electrical conductivities and thus are the most difficult test of the MCP method. Much higher MCP sensitivity has been seen detecting cracks in aluminum specimens.

C. Details of EDM Notch Detection on a Titanium Standard

FIG. 5 shows a surface EDM notch standard made by NDT Engineering. Three EDM notches are fabricated on the standard. Their dimensions are:
  a. Notch A:—0.100" (L)×0.022" (D);
  b. Notch B:—0.060" (L)×0.022" (D);
  c. Notch C:—0.030" (L)×0.016" (D).

The MCP test results for detection of notches B and C on this standard made by NDT Engineering are shown in FIG. 6; note the clear, unambiguous detection and localization of the two smaller notches by the early prototype MCP.

D. Details of Fatigue-Crack Detection on Titanium Specimens

FIG. 7 shows four titanium specimens with fine fatigue cracks generated on one side of each of the specimens. The specimens were made by FAA AANC at Sandia National Laboratories, Albuquerque, N. Mex. The crack sizes were measured using a microscope, as shown in FIG. 8. MCP test results on these specimens are shown in FIG. 9; again, note the clear and unambiguous detection and localization of the fatigue cracks in these test specimens.

Figure 10:
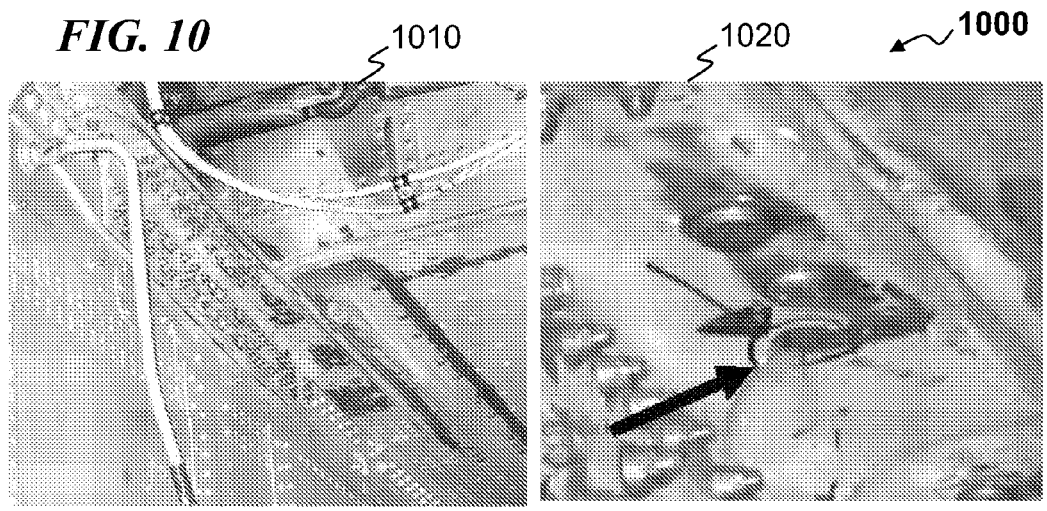
FIG. 10 is a pair of photographs 1000 of Reference Target (1)—C-130 CWB (Center Wing Box).
Figure 11:
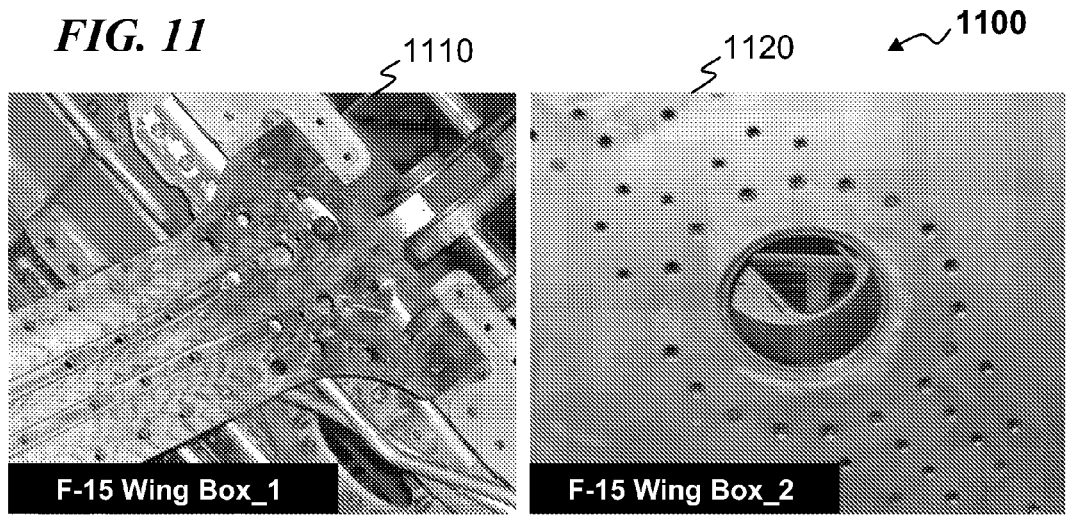
FIG. 11 is a pair of photographs 1100 of Reference Target (2)—F-15 Wing Box.

Some objectives for the invention include:
  a. Developing prototypes of new Magnetic Carpet Probes that can be used for monitoring thick, multi-layered, complex structures for the initiation and growth of cracks. Some embodiments of the present invention, for example, are used for monitoring thick, multi-layer and complex aluminum aircraft structures, which typically are assembled with aluminum or steel fasteners for the initiation and growth of cracks. FIG. 10 and FIG. 11 are two typical references of such aircraft structures.
  b. Based on the results of the prototype phase, specifying and developing a new MCP and system that will meet the following requirements:
    1) High sensitivity—Capable of detecting crack growth in aluminum material at an increment around 0.020"-0.040" and showing the crack orientation and crack-growth direction.
    2) High speed for large-area inspection/crack detection—less than ten seconds for completion of 3"×3" area inspection/crack detection.
  High reliability and repeatability in crack detection.
    3) In-situ calibration.
    4) Robustness—can be embedded in the harsh environment required by aircraft applications.
    5) Simple in use—can fit the requirements for depot-level applications.
    6) Light weight, small in size, readily attached to aircraft structures.
    7) Low cost,
  c. Completing pre-commercialization prototyping of the above MCP, and being ready for production for providing products to the United States Air Force (USAF) and Federal Aviation Administration (FAA) Fleet.

The basic concept of the Magnetic Carpet Probe (MCP) for embedded sensors has been demonstrated, and the applicability, capability and reliability are being assessed in a variety of applications to FAA and USAF components, assemblies and structures. NDI involves the indirect measurement of a desired property or characteristic (test object condition—TOC) by relating variations in the desired material property/characteristics to a NDI measurement. The development and application sequence involves:
  a. Establishment of a reproducible NDI measurement system based on selected "calibration" conditions or artifacts.
  b. Establishing a causal-model relationship between variations in the NDI measurements and variations in the test-object condition (TOC). Although cracks are not the only condition that can be assessed, for purposes of discussion, we will use crack length as the TOC scalar detection requirement.
  c. Assuring that the measured outputs are above the responses from normal variances in the test-object conditions (normal material-response variations that are below the required crack-detection threshold).
  d. Assuring that the NDI measurement response has significant gain increase with an increase in crack length to enable discrimination of small cracks from large cracks.
  e. Establish an NDI signal-response level (NDI acceptance threshold) that can be used as a basis for acceptance to meet structural-integrity requirements for continuing aircraft service.

This constitutes the FIRST STEP in demonstrating that an NDI method may be applicable to meet an aircraft-structure-acceptance requirement and in the development of an inspection procedure. The SECOND STEP is to qualify and validate the applicability and discrimination level of the method for application.

The task of qualifying and validating an NDI method requires both experimental rigor and engineering analyses to assure that a high confidence can be established for the NDI method and procedure in various intended applications. This involves:
  a. REPRODUCIBILITY DEMONSTRATION—Reproducibility is demonstrated by repetitive calibration and measurement of multiple artifacts that are candidates for use in production calibration. A small variance in output is required before the procedure is considered for further development.

b. APPLICATION VARIANCE ANALYSES—A probability-of-detection (POD) measurement metric is generally used to assess and quantify the effects of various application variables in the NDI measurements procedure. A list of possible application variables is made and the effects (significance of variance) of variables are assessed by the POD metric. This may be accomplished by systematically holding application parameters constant and assessing potential variables on a case-by-case basis. The approach to be initially assessed in some embodiments includes principles of "DESIGN OF EXPERIMENT" to quickly assess the potential significance of multiple variables using a matrix-analysis method—DICE INSTEAD OF SLICE. For example, the proximity of the sensor array in the Magnetic Carpet Probe (MCP) with respect to a crack edge and crack tip are characterized and the effects quantified in detail, while the effects of multiple-calibration variance is expected to be small (insignificant with respect to other variances). Significant variables and variances identified are then quantified in validation analyses.

c. VALIDATION—Finally, the system response is characterized using actual aircraft anomalies to validate detection capability and applicability in each intended application.

FIG. 10 is a pair 1000 of photographs of Reference Target (1)—C-130 CWB (Center Wing Box). Photograph 1010 shows the general area, with numerous bolts, nuts, and rivet heads near a right-angle joint between a vertical wall at the lower left and a horizontal structure at the upper right. A small arrow at the center of photograph 1010 shows the area of interest, and the photograph as a whole shows the very difficult environment in which to diagnose a fault. Photograph 1020 is an enlargement of the center portion of the center of photograph 1010 showing more detail of the area of interest, and the photograph as a whole shows the very difficult environment in which to diagnose a fault. In some embodiments, an MCP system 300 using a circularly symmetric arrangement of coils 1200 (such as schematically shown in FIG. 12) placed or adhered (in some embodiments, the flex substrate 200 includes an adhesive surface that can be used to removeably affix the flex substrate 200 to the OUI 99) centered on the circular structure at the end of the arrow can detect radial cracks or other buried anomalies.

FIG. 11 is a pair of photographs of Reference Target (2)—F-15 Wing Box. Photograph 1110 shows the general area, with numerous holes, bolts, nuts, and rivet heads near a rotating joint between a structure extending to the lower left and a pin at the upper right. Photograph 1120 is a close-up view of another portion. Again, in some embodiments, an MCP system 300 using a circularly symmetric arrangement of coils 1200 (such as schematically shown in FIG. 12) can be placed or adhered centered on the circular opening of photograph 1120, or around the pin of photograph 1110.

FIG. 12 is a block diagram of a radial layout of an MCP 1200 for structural monitoring and crack detection near a hole with a fastener. In some embodiments, a plurality of MCP sensor-element coils 1221 (on or more coils 1221 per box (e.g., of the three circumferential rows of eight boxes each)) is symmetrically arranged around a fastener or hole. In other embodiments, an arrangement of a plurality of coils is placed around an irregular boundary to be diagnosed. In some embodiments, the MCP for detecting and monitoring cracks initiating from a fastener hole and propagating in the vicinity of the fastener has a radial layout similar to that shown in FIG. 12.

FIG. 13 is a block diagram of a rectilinear layout of an MCP 1300 for structural monitoring and crack detection of an area without a fastener or other obstruction, wherein a plurality of MCP sensor-element coils 1321 are formed in an array on the flex substrate 200. In other embodiments, the array of coils can be in any other suitable configuration, such as a hexagonal, triangular, or other geometric shape. In some embodiments, the MCP for detecting and monitoring cracks initiating from an area without a fastener, but possibly with geometrical variations, will have a rectilinear layout similar to that shown in FIG. 13.

FIG. 14 is a schematic block diagram of an apparatus 100 having a sensor that includes a plurality of excitation/sensing coils that are electronically scanned to determine a position of a defect in a surface of an object. In some embodiments, apparatus 1400 includes an eddy-current detection-and-display system 330 (e.g., an SSEC system), such as the super-sensitive eddy-current system described in U.S. Pat. No. 6,636,037, and a probe control unit 120 connected to a plurality of excitation/sensing coils 129 used to scan an object-under-test 99 (e.g., a metal object under inspection). In some embodiments, probe control unit 120 includes a programmable-logic control chip 123 (such as a model XC9500 available from Xilinx), that runs or controls an analog switch 122 (such as a triple SPDT switch part number ADG733 available from Analog Devices) and/or one or more analog multiplexers 121 (such as one or more 32:1 mux part number ADG732, available from Analog Devices). These analog switches or muxes connect a selected one of the excitation/sensing coils 129 to the eddy-current detection-and-display system 101 and connect a reference coil 125 to a differential circuit, such as described in FIG. 15. In some embodiments, one or more of the mux outputs are connected to calibration coils 127 that can be used to calibrate the signals obtained from a test coil. In some embodiments, a nulling coil 126 can be switched for the reference coil 125. In some embodiments, a plurality of calibration coils 127 are used, each attached to or adjacent to a calibration piece of metal (e.g., different thicknesses or having different defects, cracks, pits, or other anomalies), and each is tested and a calibration result is stored in a memory of eddy-current detection-and-display system 101. In some embodiments, each of the excitation/sensing coils 129 in coil portion 110 is connected through mux 121 in a predetermined sequence that scans the area of object 99 that is under the array of excitation/sensing coils 129. In some embodiments, a monitor in SSEC 330 displays the results of the scan as heights and/or colors referenced to an area corresponding to the array of excitation/sensing coils 129. In some embodiments, a gain module 124 is also included to further amplify the sensed signals.

Figure 15:
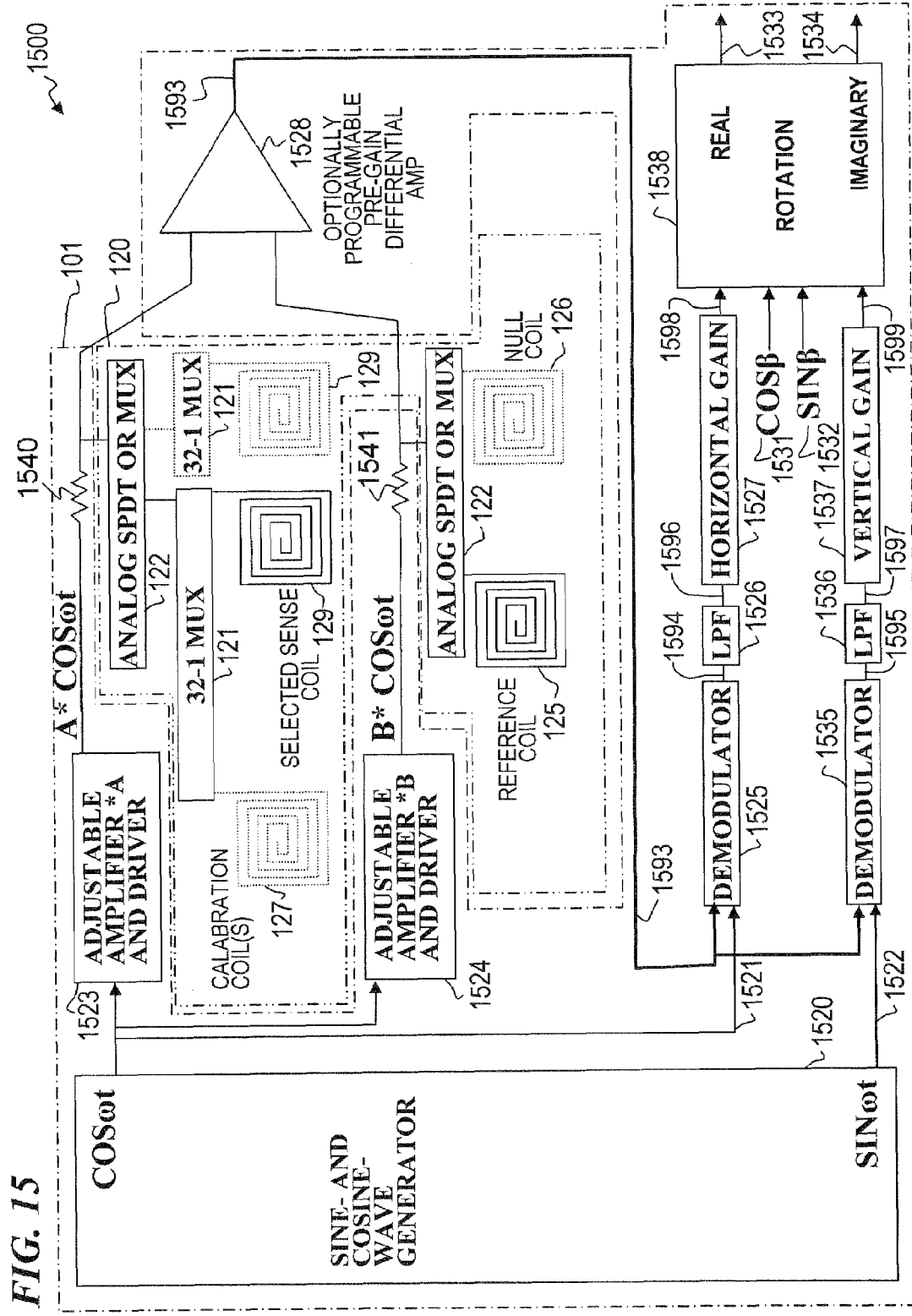
FIG. 15 is a schematic block diagram of the excitation driver and sensing demodulator 1500 of apparatus 1400.

FIG. 15 is a schematic block diagram of the excitation driver and sensing demodulator 1500 of apparatus 100. In some embodiments, eddy-current detection-and-display system 101 includes a sine-wave and cosine-wave generator 1520 that outputs sine and cosine versions of a wave having a selected frequency useful for scanning the object 99 (e.g., selected for the type of metal and its configuration and thickness). In some embodiments, the cosine($\omega$t) signal 1521 is buffered through adjustable amplifier 1523 having an amplification factor A, and the resulting signal A*cosine($\omega$t) is connected through an impedance (such as the resistance 1540 shown, or another suitable impedance such as one including resistance, capacitance, and/or inductance) to a selected coil 129 through analog switch 122 and/or mux 121, and the selected coil 129 is also connected to one input of differential amplifier 1528. In some embodiments, the cosine(ωt) signal is also buffered through adjustable amplifier 1524 having an amplification factor B, and the resulting signal B*cosine(ωt) is connected through an impedance (such as the resistance 1541 shown, or another suitable impedance such as one including resistance, capacitance, and/or inductance) to a selected reference coil 125 through analog switch 122 (and/or a mux, not shown), and the reference coil 125 is also connected to one input of differential amplifier 1528. The differential amplifier outputs a difference signal that represents the difference between the selected sense coil 129 and the selected reference coil 125. The difference signal is mixed (i.e., multiplied) by demodulator 1525 with the cosine(ωt) signal 1521, then goes through low-pass filter 1526 and H gain amplifier 1527, and represents a signal having real and imaginary components based on the phase and amplitude changes of the selected sense coil 129. The difference signal is also mixed (i.e., multiplied) by demodulator 1535 with the sine(ωt) signal 1522, then goes through low-pass filter 1536 and V gain amplifier 1537, and represents a signal having real and imaginary components based on the phase and amplitude changes of the selected sense coil 129. These two signals are then processed by rotator 1538 which has input factors cosine (beta) and sine(beta) that are used to isolate or separate the real and imaginary components, which are then output as real component 1533 and imaginary component 1534.

In other embodiments, the sine-wave and cosine-wave generator 1520 includes a plurality of phases (e.g., plus 0 degrees (the present two outputs 1521 and 1522), and also plus 30 degrees, plus 60 degrees, etc.) for each of the cosine(ωt) signal 1521 and sine(ωt) signal 1522 and a corresponding plurality of each of the other electrical components, in order to generate a traveling magnetic wave by having successive phases in neighboring coils. (See the other patents and applications by the present inventors U.S. Pat. No. 6,636,037 and U.S. patent application Ser. No. 11/114,507 (now U.S. Pat. No. 7,301,335) which are incorporated herein by reference, for more details regarding traveling magnetic wave probes and testing.) This traveling wave technology provides the sensing capabilities of a moving probe without having to move the probe or deal with noise issues that arise when moving the probe.

Figure 16:
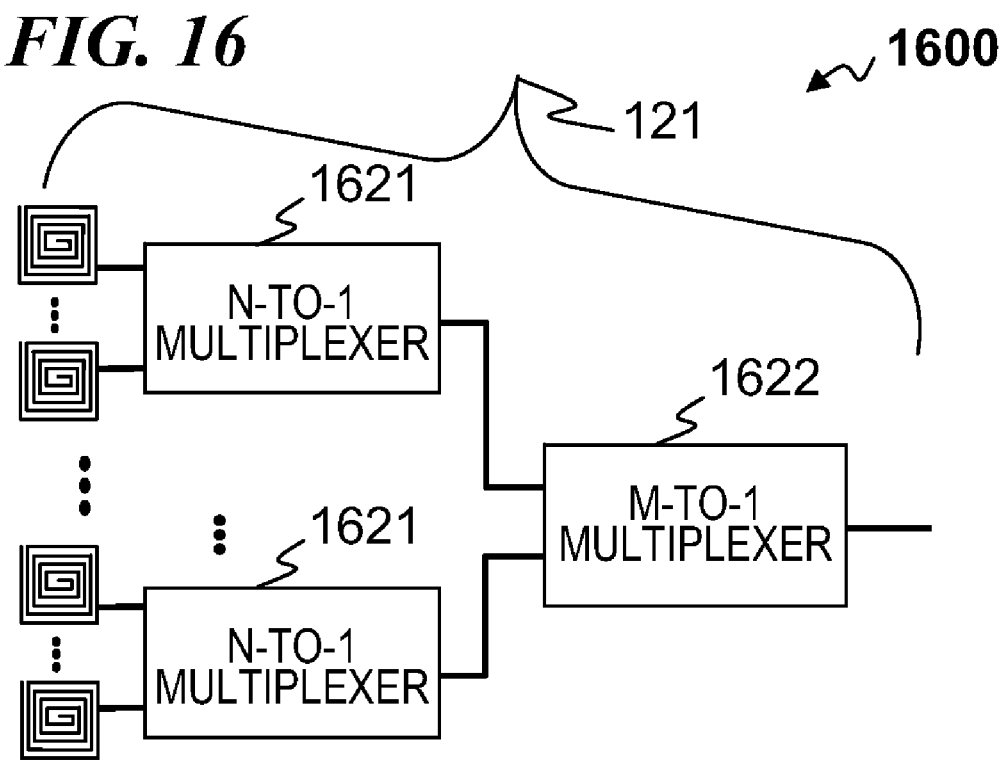
FIG. 16 is a schematic diagram 1600 of a cascaded multiplexer that is used in some embodiments of the present invention.

FIG. 16 is a schematic diagram of a cascaded multiplexer 1600 (including up to M N-to-one muxes 1621 connected to an M-to-one mux 1622) that is used in some embodiments of the present invention in place of a mux 121 described above. One or more cascaded stages of analog multiplexer and/or analog switch can be thus used to obtain an arbitrary large number of coil outputs (e.g., a thirty-two-to-one (32:1) mux 1622 driving 32 other 32:1 muxes 1621 allows the circuit to drive 1024 coils; additional stages or muxes having larger fanouts can drive even more coils).

FPGA or CPLD are Typical Programmable Chips.

In some embodiments, for example, the ADG733 part (from Analog Devices, Inc.) is a low-voltage, CMOS device having three independently selectable SPDT (single pole, double throw) switches, low power consumption and operating supply range of +1.8 V to +5.5 V and dual ±3 V. All channels exhibit break before make switching action preventing momentary shorting when switching channels. An input is used to enable or disable the device. When disabled, all channels are switched off.

The ADG732 is a monolithic CMOS 32-channel analog multiplexers that switches one of thirty-two inputs (S1-S32) to a common output, D, as determined by the 5-bit binary address lines A0, A1, A2, A3 and A4.

The XILINX XC9500 CPLD family includes low-cost programmable-logic devices with a wide array of packages and a library of application notes. They can be programmed to generate logic control signals needed. In the present invention these signals include:

a. multiplexer timing signals for scanning consequence of coils in coil array;
b. signals for working in differential mode, connecting to reference coil;
c. for working in nulling mode, connecting to nulling coil if it is desired for the null point to appear at the center of the screen, or connecting to a particular coil element if it is desired for the signal from the particular coil to appear at the center of screen.
d. scan area selection—assign special coil column numbers and row numbers for zoom-in scan, etc.

In some embodiments, a device such as device 300 (using a sixty-four-to-one mux 121) of FIG. 3 is used for the case when number of coils equals 64. When the number of coils used (M*N) is larger or different than 64, a general multiple-level multiplexer structure 1600 can be used, such as shown in diagram 1600.

In some embodiments, these designs are based on the estimated tradeoffs between sensor size, sensor density, circuit complexity for the target applications, and manufacturability issues. In some embodiments, circuit performance is evaluated with respect to design calculations and test requirements, and circuit design is iterated as necessary. Among the issues explored at this stage are the engineering tradeoffs between individual sensor size and sensor density in the sensor array; while sensor sensitivity increases with the size of the individual sensor, the increased spatial averaging of larger sensors can reduce spatial discrimination, requiring careful balancing of these design constraints with respect to the specific application.

As these engineering compromises between sensor size and density are intimately linked with the algorithms used for crack identification and localization, systems software will be iterated and optimized in parallel with sensor development.

Final design of prototype MCPs for the target applications will be established based on results of the above design iterations. Final design iterations on the signal processing algorithms will be integrated into a new version of the SSEC system, incorporating modifications specific to the target applications. The crack identification and information displays may also be revised at this point, incorporating knowledge gained during this development cycle.

In some embodiments, at least one target retired airplane, or a coupon from a retired airplane, is identified for initial test of MCP applications. A number of structural areas of interest are identified for crack detection and growth monitoring using MCPs. The test structures are analyzed to determine any special test requirements, and establish test standards for these structures. The MCP and FPCB design are refined to meet the requirements of these real world applications. A monitoring system is designed that connects and controls all the MCPs to be installed on the target airplane/coupon. The SSEC system is modified as needed to incorporate networking capabilities necessary to function with the monitoring system. Prototypes of the revised FPCBs and MCPs are fabricated. The performance of these prototypes is tested in the laboratory. The prototypes are attached on the areas of interest of the target airplane/coupon, and the monitoring system is installed. A pre-application test of the monitoring system and the installed sensors is performed. The pre-application test results of the networked system of sensors are analyzed, and the sensors and monitoring system are modified as required. The test procedure is performed, and results analyzed against the established test standards.

Incremental aircraft costs associated with the addition of MCP sensor networks are expected to be minimal, relative to the overall cost of the aircraft, thus providing a cost-effective means of safely extending aircraft lifetime.

The first step in commercializing MCP technology is to identify the initial applications for commercialization, i.e., structures with the potential for high payback from embedded testing. These would include structures which are highly stressed and subject to catastrophic failure, and which could be difficult to test with present technologies, e.g., multilayer structures in which regions of interest were encapsulated and inaccessible, and would be identified in cooperation with the representatives of the FAA, the USAF and AFRL (Air Force Research Lab).

After selection of the target aircraft, a detailed commercialization plan will be developed based on the knowledge gained developing prototype arrays. While it is impossible to predict at this early stage the exact details of this process, it will begin with design of sensor arrays for the structural locations to be monitored. The overall system would be designed so that multiple sensor array configurations could be operated by a standard design control unit, with software modifications as needed. This would reduce the overall time and expense of building sensors for a wide variety of structure geometries to be monitored.

After initial development of basic sensor formats, e.g., for flat surfaces, stepped surfaces, singly and multiply-curved surfaces, round shafts, etc., custom sensor arrays for specific target structures could be designed and prototyped, with full production following after prototype qualification. Production would use well established, conventional flexible-circuit manufacturing methods, and facilities would be sized to meet projected volumes. Interconnection of multiple sensor arrays with a standard control unit, and networking throughout an aircraft, or portion of an aircraft, would require design of a network controller and determination of an interconnect architecture; the noise in a military aircraft would probably preclude use of wireless networking, and might require noise shielding or optical networking. The network architecture would be driven by the target application, but could be either a single bus running the length of a structure, e.g., a wing section or a fuselage, with sensors stubbed off at the desired monitoring locations, or else a network of individually connected sensor units in more complicated structures.

If MCP technology were included in the original design of the aircraft, the sensor network could be embedded within multilayer structures, allowing, for example, remote monitoring of metal layers buried in composites, but this is not envisioned for the initial commercialization. Target pricing for network controllers and interconnect circuits would of course be determined network complexity, but is expected to be small compared to the overall cost of the structures to be monitored, and thus supportable in light of both increased structural lifetimes and increased confidence in overall aircraft safety.

Design and development of sensor networks will allow instrumentation of a test group of target aircraft, from which qualification data can be gathered towards the ultimate goal of flight certification. Standards for test certification and the length of the qualification process will be developed in cooperation with the FAA, the USAF, and AFRL. In parallel, sensor robustness will be evaluated as experience is gained with a larger device population over extended times in the target environment, and the sensor industrial design will be adapted as required to increase lifetimes to the desired level.

Certification of the MCP technology for aircraft monitoring and crack detection would allow the technology to be offered for sale to present owners of aircraft, and to aircraft suppliers; ongoing work would include designing sensor networks for individual target aircraft, and tailoring sensor configurations to their unique structures, providing an ongoing, sustainable business model to support long term commercialization of MCP aircraft monitoring.

Innovative Materials Testing Technologies, Inc. (IMTT), the assignee of the present invention, has built an early prototype MCP for aircraft-engine applications: the MCP V1-2 discussed above. This device has shown high sensitivity and speed of operation in detecting fine cracks on titanium test specimens. Titanium materials have very low electric conductivities and thus are the most difficult test of the MCP approach to crack detection. In some embodiments, MCP methods are applied to detecting cracks in aluminum structures that have much higher conductivity, resulting in the higher MCP sensitivity that has been observed in preliminary testing of aluminum specimens with the present device.

The prototype FPCB on which the MCP V1-2 is based incorporates advanced, fine-scale circuit methods (e.g., such as those available from MicroConnex) to produce the required array of multi-layer coil structures, integrated with all necessary power and data connections. MCPs are purely electronic devices and systems, and thus avoid the problems and expense inherent in mechanical/acoustical test methods. As such, MCPs are suited to meet the need for high reliability in an embedded aircraft application, and will have a lower cost than competing acoustical methods, which require expensive piezoelectric transducers and support circuitry, and which are inherently more fragile, and must operate under a narrower range of environmental conditions. In some embodiments, optimization of MCP sensor size, density and geometry for target applications, as well as optimization of MCP layout and construction to provide conformation to complex, non-planar geometries, optimization of crack-detection algorithms to achieve maximum performance with revised MCP sensor arrays in the target applications, development of attachment methods to ensure high reliability of an MCP embedded in harsh aircraft environments, and revision of crack-reporting methods to meet the specific requirements of the target user group of depot operators, etc., are obtained by testing and empirical determination.

Some embodiments include an apparatus that includes a sensor unit having a plurality of electromagnetic coils; an excitation/sensing circuit that generates an AC excitation signal; and a multiplexer that electrically connects a first coil selected from the plurality of coils through a predetermined impedance to the AC excitation signal; the excitation/sensing circuit is configured to demodulate a first signal from the first coil in order to detect phase and/or amplitude changes due to a magnetic anomaly of an object being scanned.

Some embodiments further include a reference coil, in which the excitation/sensing circuit includes a differential amplifier, and at some first period of time the first coil is selectively connected to a first input of the differential amplifier and the reference coil is connected to a second input of the differential amplifier.

In some embodiments, at some second period of time, a second coil selected from the plurality of coils is connected by the multiplexer to the AC excitation signal, and is selectively connected to the first input of the differential amplifier and the reference coils is connected to the second input of the differential amplifier.

Some embodiments further include a first demodulator that includes a first mixer and low-pass filter coupled to receive a first-phase version (e.g., cosine($\omega$t)) of the AC excitation signal and to receive an output signal from the differential amplifier, and to output a first demodulated signal; and a second demodulator that includes a second mixer and low-pass filter coupled to receive a second-phase version (e.g., sine($\omega$t)) of the AC excitation signal and to receive the output signal from the differential amplifier, and to output a second demodulated signal.

Some embodiments further include a rotator that is operatively coupled to receive the first demodulated signal and the second demodulated signal, and to generate output signals representative of real and imaginary portions of a sensed signal from the first coil at the first period of time, and to generate output signals representative of real and imaginary portions of a sensed signal from the second coil at the second period of time.

Some embodiments further include a graphical output driver configured to generate an output display signal for a monitor to display a graphical representation showing magnetic anomalies as a function of position.

In some embodiments, the plurality of coils is arranged in a two-dimensional array, and the output display signal causes a display of magnetic anomalies relative to an area corresponding to the array.

In some embodiments, the plurality of coils is arranged in a two-dimensional rectangular array, and the output display signal causes a display of magnetic anomalies relative to an area corresponding to the rectangular array.

Some embodiments further include a first calibration coil located adjacent to a calibration piece of material similar in construction to the object being scanned, and the multiplexer is configured to couple the first calibration coil to the AC excitation signal and the first input of the differential amplifier; and a storage unit operatively coupled to store a calibration value each based on a measurement using the first calibration coil.

Some embodiments further include a plurality of calibration coils, each one of the plurality of calibration coils located adjacent to a calibration piece of material similar in construction to the object being scanned, and the multiplexer is configured to successively couple each one of the plurality of calibration coils to the AC excitation signal and the first input of the differential amplifier; and a storage unit operatively coupled to store a plurality of calibration values each based on a measurement using one of the calibration coils.

Some embodiments further include a method including providing a plurality of thin-film coils in an array on a substrate; selecting a first coil from the plurality of thin-film coils and establishing an analog electrical connection to the selected first coil; driving the first coil with an AC excitation signal through a first predetermined impedance and the analog multiplexer to obtain a first sensed signal; and demodulating the first sensed signal in order to detect phase and/or amplitude changes due to a magnetic anomaly of an object being scanned.

Some embodiments further include providing a reference coil, driving the reference coil with an AC excitation signal through a first predetermined impedance to obtain a reference signal; and the demodulating of the first sensed signal includes differentially amplifying the reference signal relative to the first sensed signal to obtain a differential signal at some first period of time.

Some embodiments further include at some second period of time, selecting a second coil from the plurality of coils; driving the second coil with the AC excitation signal through a second predetermined impedance to obtain a second sensed signal; and differentially amplifying the reference signal relative to the second sensed signal to obtain a differential signal at some second period of time.

Some embodiments further include mixing and low-pass filtering a first-phase version (e.g., cosine($\omega$t)) of the AC excitation signal with an output signal from the differential amplifier, and outputting a first demodulated signal; and mixing and low-pass filtering a second-phase version (e.g., sine($\omega$t)) of the AC excitation signal with the output signal from the differential amplifier, and outputting a second demodulated signal.

Some embodiments further include rotating the first demodulated signal and the second demodulated signal to generate output signals representative of real and imaginary portions of a sensed signal from the first coil at the first period of time, and to generate output signals representative of real and imaginary portions of a sensed signal from the second coil at the second period of time.

Some embodiments further include generating an output display signal for a monitor to display a graphical representation showing magnetic anomalies as a function of position.

In some embodiments, the plurality of coils is arranged in a two-dimensional array, and the output display signal causes a display of magnetic anomalies relative to an area corresponding to the array.

In some embodiments, the plurality of coils is arranged in a two-dimensional rectangular array, and the output display signal causes a display of magnetic anomalies relative to an area corresponding to the rectangular array.

Some embodiments further include providing a first calibration coil located adjacent to a calibration piece of material similar in construction to the object being scanned; coupling the first calibration coil to the AC excitation signal and the first input of the differential amplifier; and storing a calibration value each based on a measurement using the first calibration coil.

Some embodiments further include providing a plurality of calibration coils, each one of the plurality of calibration coils located adjacent to a calibration piece of material similar in construction to the object being scanned; successively coupling each one of the plurality of calibration coils to the AC excitation signal and the first input of the differential amplifier; and storing a plurality of calibration values each based on a measurement using one of the calibration coils.

Some embodiments include an apparatus that includes a plurality of thin-film coils in an array on a substrate; means for selecting a first coil from the plurality of thin-film coils and establishing an analog electrical connection to the selected first coil; means for driving the first coil with an AC excitation signal through a first predetermined impedance and the analog multiplexer to obtain a first sensed signal; and means for demodulating the first sensed signal in order to detect phase and/or amplitude changes due to a magnetic anomaly of an object being scanned.

Some embodiments further include means for providing a reference coil, means for driving the reference coil with an AC excitation signal through a first predetermined impedance to obtain a reference signal; and the demodulating of the first sensed signal includes differentially amplifying the reference signal relative to the first sensed signal to obtain a differential signal at some first period of time.

Some embodiments further include means for selecting, at some second period of time, a second coil from the plurality of coils; means for driving the second coil with the AC excitation signal through a second predetermined impedance to obtain a second sensed signal; and means for differentially amplifying the reference signal relative to the second sensed signal to obtain a differential signal at some second period of time.

Some embodiments further include means for mixing and low-pass filtering a first-phase version (e.g., cosine(ωt)) of the AC excitation signal with an output signal from the differential amplifier, and outputting a first demodulated signal; and means for mixing and low-pass filtering a second-phase version (e.g., sine(ωt)) of the AC excitation signal with the output signal from the differential amplifier, and outputting a second demodulated signal.

Some embodiments further include means for rotating the first demodulated signal and the second demodulated signal to generate output signals representative of real and imaginary portions of a sensed signal from the first coil at the first period of time, and to generate output signals representative of real and imaginary portions of a sensed signal from the second coil at the second period of time.

Some embodiments further include means for generating an output display signal for a monitor to display a graphical representation showing magnetic anomalies as a function of position.

In some embodiments, the plurality of coils is arranged in a two-dimensional array, and the output display signal causes a display of magnetic anomalies relative to an area corresponding to the array.

In some embodiments, the plurality of coils is arranged in a two-dimensional rectangular array, and the output display signal causes a display of magnetic anomalies relative to an area corresponding to the rectangular array.

Some embodiments further include means for providing a first calibration coil located adjacent to a calibration piece of material similar in construction to the object being scanned; means for coupling the first calibration coil to the AC excitation signal and the first input of the differential amplifier; and means for storing a calibration value each based on a measurement using the first calibration coil.

Some embodiments further include means for providing a plurality of calibration coils, each one of the plurality of calibration coils located adjacent to a calibration piece of material similar in construction to the object being scanned; means for successively coupling each one of the plurality of calibration coils to the AC excitation signal and the first input of the differential amplifier; and means for storing a plurality of calibration values each based on a measurement using one of the calibration coils.

It is understood that the above description is intended to be illustrative, and not restrictive. Many other embodiments will be apparent to those of skill in the art upon reviewing the above description. The scope of the invention should, therefore, be determined with reference to the appended claims, along with the full scope of equivalents to which such claims are entitled. In the appended claims, the terms "including" and "in which" are used as the plain-English equivalents of the respective terms "comprising" and "wherein," respectively. Moreover, the terms "first," "second," "third," and the like are used merely as labels, and are not intended to impose numerical requirements on their objects

What is claimed is:

1. An apparatus comprising:
a sensor unit having a plurality of electromagnetic sensing coils;
an excitation/sensing circuit that generates an AC excitation signal, wherein the excitation/sensing circuit includes a differential amplifier;
a plurality of reference coils including a first reference coil and a second reference coil, wherein the first reference coil is configured for a first type of metal and the second reference coil is configured for a second type of metal different from the first type;
a first circuit that includes a multiplexer that at some first period of time electrically connects a first sensing coil selected from the plurality of sensing coils to a first input of the differential amplifier and through a predetermined impedance to the AC excitation signal; and
a second circuit that at the first period of time selectively connects one of the plurality of reference coils to a second input of the differential amplifier, wherein the excitation/sensing circuit is configured to demodulate a first signal from the first sensing coil and the first reference coil in order to detect a phase change, an amplitude change, or both phase and amplitude changes due to a magnetic anomaly of an object being scanned.

2. The apparatus of claim 1,
wherein at some second period of time the second reference coil selected from the plurality of reference coils is selectively connected to the second input of the differential amplifier.

3. The apparatus of claim 1, further comprising:
a first calibration coil located adjacent to a calibration piece of material similar in construction to the object being scanned, wherein the multiplexer is configured to couple the first calibration coil to the AC excitation signal and the first input of the differential amplifier; wherein the apparatus is configured to be calibrated based on a measurement taken using the first calibration coil.

4. The apparatus of claim 1, further comprising:
a plurality of calibration coils, each one of the plurality of calibration coils located adjacent to a calibration piece of material similar in construction to the object being scanned, wherein the multiplexer is configured to successively couple each one of the plurality of calibration coils to the AC excitation signal and the first input of the differential amplifier, wherein the apparatus is configured to be calibrated based on measurements taken using the plurality of calibration coils.

5. An apparatus comprising:
a sensor unit having a plurality of electromagnetic coils;
an excitation/sensing circuit that generates an AC excitation signal, wherein the excitation/sensing circuit includes a differential amplifier;
a multiplexer that, at a first period of time, selectively electrically connects a first coil selected from the plurality of coils through a first predetermined impedance to the AC excitation signal; and
a source of a first reference signal,
wherein at the first period of time the first coil is selectively connected to a first input of the differential amplifier and the first reference signal is connected to a second input of the differential amplifier,
wherein at some second period of time, a second coil selected from the plurality of coils is selectively connected by the multiplexer to the AC excitation signal through the first predetermined impedance, and is selectively connected to the first input of the differential amplifier and the first reference signal is connected to the second input of the differential amplifier, and
wherein the excitation/sensing circuit is configured to demodulate a first signal from the first coil in order to detect phase and/or amplitude changes due to a magnetic anomaly of an object being scanned.

6. The apparatus of claim 5, where the source of the first reference signal includes a reference coil.

7. The apparatus of claim 5, wherein the sensor unit having the plurality of electromagnetic coils is formed as a thin-film two-dimensional array of coils on a flexible substrate that is configured to be placed in a substantially fixed position relative to a metallic object during inspection of a two-dimensional area of the object such that each respective coil of the plurality of coils measures an electromagnetic condition of a portion of the two-dimensional area of the metallic object adjacent that respective coil.

8. The apparatus of claim 5, wherein the sensor unit having the plurality of electromagnetic coils is formed as a thin-film array of coils on a flexible substrate that is configured to be placed in a substantially fixed position relative to a metallic object during inspection of an area of the object such that each respective coil of the plurality of coils measures an electromagnetic condition of a portion of the area of the metallic object adjacent that respective coil, and wherein the array of coils is arranged across a first dimension and a second dimension of the flexible substrate.

9. The apparatus of claim 5, wherein an output signal of the differential amplifier is $E*\cosine(\omega t+\alpha)$, wherein E is a magnitude and $\alpha$ is a phase-shift due at least in part to the magnetic anomaly of an object being scanned,
the apparatus further comprising:
   a first demodulator that includes a first mixer and low-pass filter coupled to receive a first signal $\cosine(\omega t)$ representing a first-phase version of the AC excitation signal and to receive the output signal $E*\cosine(\omega+\alpha)$ from the differential amplifier, and to output a $K*\cosine(\alpha)$ signal representing a real component of a demodulated signal; and
   a second demodulator that includes a second mixer and low-pass filter coupled to receive a second signal $\sine(\omega t)$ representing a second-phase version of the AC excitation signal and to receive the output signal $E*\cosine(\omega+\alpha)$ from the differential amplifier, and to output a signal $K*\sine(\alpha)$ signal representing an imaginary component of the demodulated signal.

10. The apparatus of claim 9, further comprising:
a rotator that is operatively coupled to receive the outputted real component of the demodulated signal and the outputted imaginary component of the demodulated signal, and to generate output signals representative of real and imaginary portions of a sensed signal at the first period of time based on the signal from and first reference signal wherein the sensed signal has been rotated relative to the demodulated signal by a rotation angle $\beta$, and to generate output signals representative of real and imaginary portions of a sensed signal at the second period of time based on the signal from the second coil and first reference signal wherein the sensed signal at the second period of time has been rotated relative to the demodulated signal by a rotation angle $\beta$.

11. The apparatus of claim 10, further comprising:
a graphical output driver configured to generate an output display signal for a monitor to display a graphical representation showing magnetic anomalies as a function of position, wherein the graphical representation is based on geometrical locations of the plurality of coils in the coil array.

12. The apparatus of claim 11, wherein the plurality of coils is arranged in a two-dimensional array, and wherein the output display signal causes a display of magnetic anomalies relative to an area corresponding to the array.

13. The apparatus of claim 11, wherein the plurality of coils is arranged in a two-dimensional rectangular array, and wherein the output display signal causes a display of magnetic anomalies relative to an area corresponding to the rectangular array.

14. The apparatus of claim 10, further comprising:
a first calibration coil located adjacent to a calibration piece of material similar in construction to the object being scanned, wherein the multiplexer is configured to couple the first calibration coil to the AC excitation signal and the first input of the differential amplifier; and
a storage unit operatively coupled to store a calibration value based on a measurement using the first calibration coil.

15. The apparatus of claim 10, further comprising:
a plurality of calibration coils, each one of the plurality of calibration coils located adjacent to a calibration piece of material similar in construction to the object being scanned, wherein the multiplexer is configured to successively couple each one of the plurality of calibration coils to the AC excitation signal and the first input of the differential amplifier; and
a storage unit operatively coupled to store a plurality of calibration values each based on a measurement using one of the calibration coils.

16. A method comprising:
providing a plurality of thin-film sensing coils in an array on a substrate;
providing a plurality of thin-film reference coils;
selecting a first sensing coil from the plurality of thin-film sensing coils and establishing an analog electrical connection to the selected first sensing coil;
driving the first sensing coil with an AC excitation signal through a first predetermined impedance to obtain a first sensed signal;
selecting a first one of the plurality of reference coils and at a first period of time, establishing an analog electrical connection to the selected first reference coil and driving the first reference coil with an AC excitation signal through a second predetermined impedance to obtain a first reference signal;
demodulating the first sensed signal, wherein the demodulating of the first sensed signal includes differentially amplifying a difference between the first sensed signal and the first reference signal at the first period of time in order to detect a phase change, an amplitude change, or both phase and amplitude changes due to a magnetic anomaly of an object being scanned; and
selecting, and at a second period of time, driving a second reference coil with an AC excitation signal through the second predetermined impedance to obtain a second reference signal; and wherein the demodulating of the first sensed signal includes differentially amplifying the second reference signal relative to the first sensed signal to obtain a differential signal at the second period of time.

17. A method comprising:
providing a plurality of thin-film coils in an array on a substrate formed as a thin-film two-dimensional array of coils on a flexible substrate;
placing the thin-film array in a substantially fixed position on a metallic object during inspection of a two-dimensional area of the object such that each respective coil of the plurality of coils measures an electromagnetic condition of a portion of the two-dimensional area of the metallic object adjacent that respective coil;
selecting a first coil from the plurality of thin-film coils and establishing an analog electrical connection to the selected first coil;

driving the first coil with an AC excitation signal through a first predetermined impedance to obtain a first sensed signal;

obtaining a first reference signal;

demodulating the first sensed signal in order to detect phase and/or amplitude changes due to a magnetic anomaly of an object being scanned, wherein the demodulating of the first sensed signal includes differentially amplifying the first reference signal relative to the first sensed signal to obtain a differential signal at some first period of time;

at some second period of time, selecting a second coil from the plurality of coils;

driving the second coil with the AC excitation signal through the first predetermined impedance to obtain a second sensed signal; and differentially amplifying the first reference signal relative to the second sensed signal to obtain a differential signal at some second period of time.

18. The method of claim 17, the demodulating further comprising:

mixing and low-pass filtering a cosine($\omega t$)-phase version of the AC excitation signal with an output signal from the differential amplifier, and outputting a real component of a demodulated signal; and mixing and low-pass filtering a sine ($\omega t$)-phase version of the AC excitation signal with the output signal from the differential amplifier, and outputting an imaginary component of the demodulated signal, wherein the real and imaginary demodulated components of the demodulated signal are two components of a demodulated signal.

19. The method of claim 18, further comprising:

rotating the demodulated signal by a preset rotation angle beta to generate output signals representative of real and imaginary portions of a sensed signal from the difference of the signal from the first coil and first reference signal at the first period of time, wherein the sensed signal has been rotated relative to the demodulated signal by the rotation angle beta during the first period of time, and to generate output signals representative of real and imaginary portions of a sensed signal from the difference of the signal from the second coil and first reference signal at the second period of time, wherein the sensed signal has been rotated relative to the demodulated signal during the second period of time by the rotation angle beta.

20. The method of claim 19, further comprising:

generating an output display signal for a monitor to display a graphical representation showing magnetic anomalies as a function of position, wherein the graphical representation is based on geometrical locations of the plurality of coils in the coil array.

21. The method of claim 20, wherein the plurality of coils is arranged in a two-dimensional array, and wherein the output display signal causes a display of magnetic anomalies relative to an area corresponding to the array.

22. The method of claim 20, wherein the plurality of coils is arranged in a two-dimensional rectangular array, and wherein the output display signal causes a display of magnetic anomalies relative to an area corresponding to the rectangular array.

23. The method of claim 19, further comprising:

providing a first calibration coil located adjacent to a calibration piece of material similar in construction to the object being scanned;

coupling the first calibration coil to the AC excitation signal and the first input of the differential amplifier; and storing a calibration value based on a measurement using the first calibration coil.

24. The method of claim 19, further comprising:

providing a plurality of calibration coils, each one of the plurality of calibration coils located adjacent to a calibration piece of material similar in construction to the object being scanned;

successively coupling each one of the plurality of calibration coils to the AC excitation signal and the first input of the differential amplifier; and storing a plurality of calibration values each based on a measurement using one of the calibration coils.

25. The method of claim 17, where the obtaining of the first reference signal further includes:

providing a first reference coil; and driving the first reference coil with an AC excitation signal through a second predetermined impedance to obtain the first reference signal.

26. The method of claim 17, further comprising:

providing a plurality of thin-film reference coils;

selecting a first one of the plurality of reference coils at a first period of time, establishing an analog electrical connection to the selected first reference coil and driving the first reference coil with an AC excitation signal through a predetermined impedance to obtain the first reference signal; and demodulating the first sensed signal, wherein the demodulating of the first sensed signal includes differentially amplifying a difference between the first sensed signal and the first reference signal at the first period of time in order to detect a phase change, an amplitude change, or both phase and amplitude changes due to a magnetic anomaly of an object being scanned.

27. An apparatus comprising:

a plurality of thin-film coils in an array on a substrate;

a plurality of thin-film reference coils;

means for selecting a first sensing coil from the plurality of thin-film sensing coils and establishing an analog electrical connection to the selected first sensing coil;

means for driving the first sensing coil with an AC excitation signal through a first predetermined impedance to obtain a first sensed signal;

means for selecting a first one of the plurality of thin-film reference coils and for, at a first period of time, establishing an analog electrical connection to the selected first reference coil and for driving the first reference coil with an AC excitation signal through a second predetermined impedance to obtain a first reference signal;

means for demodulating the first sensed signal, wherein the means for demodulating the first sensed signal includes means for differentially amplifying a difference between the first sensed signal and the first reference signal at the first period of time in order to detect phase and/or amplitude changes due to a magnetic anomaly of an object being scanned; and means for selecting and for, at a second period of time, driving a second reference coil with an AC excitation signal through the second predetermined impedance to obtain a second reference signal; and wherein the means for demodulating of the first sensed signal includes means for differentially amplifying the second reference signal relative to the first sensed signal to obtain a differential signal at the second period of time.

28. An apparatus comprising:
a plurality of thin-film coils in a two-dimensional array on a substrate
means for placing the thin-film array in a substantially fixed position on a metallic object during inspection of a two-dimensional area of the object such that each respective coil of the plurality of coils measures an electromagnetic condition of a portion of the two-dimensional area of the metallic object adjacent that respective coil;
means for selecting a first coil from the plurality of thin-film coils and establishing an analog electrical connection to the selected first coil;
means for driving the first coil with an AC excitation signal through a first predetermined impedance to obtain a first sensed signal;
means for obtaining a first reference signal;
means for demodulating the first sensed signal in order to detect phase and/or amplitude changes due to a magnetic anomaly of an object being scanned, wherein
the demodulating of the first sensed signal includes differentially amplifying the first reference signal relative to the first sensed signal to obtain a differential signal at some first period of time;
means for selecting, at some second period of time, a second coil from the plurality of coils;
means for driving the second coil with the AC excitation signal through a second predetermined impedance to obtain a second sensed signal; and
means for differentially amplifying the first reference signal relative to the second sensed signal to obtain a differential signal at some second period of time.

29. The apparatus of claim 28, further comprising:
means for mixing and low-pass filtering a cosine($\omega$t)-phase version of the AC excitation signal with an output signal from the differential amplifier, and outputting a real component of demodulated signal; and
means for mixing and low-pass filtering a sine ($\omega$t)-phase version of the AC excitation signal with the output signal from the differential amplifier, and outputting an imaginary component of the demodulated signal, wherein the real and imaginary components of the demodulated signal are the two components of a demodulated signal.

30. The apparatus of claim 29, further comprising:
means for rotating the demodulated signal by a preset rotation angle beta to generate output signals representative of real and imaginary portions of a sensed signal from the difference of the signal from the first coil and first reference signal at the first period of time, wherein the sensed signal has the beta rotation angle relative to the demodulated signal during the first period of time, and to generate output signals representative of real and imaginary portions of a sensed signal from the difference of the signal from the second coil and first reference signal at the second period of time, wherein the sensed signal has been rotated relative to the demodulated signal during the second period of time by the rotation angle beta.

31. The apparatus of claim 30, further comprising:
means for generating an output display signal for a monitor to display a graphical representation showing magnetic anomalies as a function of position.

32. The apparatus of claim 31, wherein the plurality of coils is arranged in a two-dimensional array, and wherein the output display signal causes a display of magnetic anomalies relative to an area corresponding to the array.

33. The apparatus of claim 31, wherein the plurality of coils is arranged in a two-dimensional rectangular array, and wherein the output display signal causes a display of magnetic anomalies relative to an area corresponding to the rectangular array.

34. The apparatus of claim 30, further comprising:
means for providing a first calibration coil located adjacent to a calibration piece of material similar in construction to the object being scanned;
means for coupling the first calibration coil to the AC excitation signal and the first input of the differential amplifier; and
means for storing a calibration value based on a measurement using the first calibration coil.

35. The apparatus of claim 30, further comprising:
means for providing a plurality of calibration coils, each one of the plurality of calibration coils located adjacent to a calibration piece of material similar in construction to the object being scanned;
means for successively coupling each one of the plurality of calibration coils to the AC excitation signal and the first input of the differential amplifier; and
means for storing a plurality of calibration values each based on a measurement using one of the calibration coils.

36. The apparatus of claim 28, where the means for obtaining of the first reference signal further includes:
a first reference coil; and
means for driving the first reference coil with an AC excitation signal through a second predetermined impedance to obtain the first reference signal.

37. The apparatus of claim 28, further comprising:
a plurality of thin-film reference coils; and
means for selecting a first one of the plurality of thin-film reference coils and for, at a first period of time, establishing an analog electrical connection to the selected first reference coil and for driving the first reference coil with an AC excitation signal through a predetermined impedance to obtain the first reference signal;
wherein the means for demodulating the first sensed signal includes means for differentially amplifying a difference between the first sensed signal and the first reference signal at the first period of time in order to detect phase and/or amplitude changes due to a magnetic anomaly of an object being scanned.

* * * * *

UNITED STATES PATENT AND TRADEMARK OFFICE
CERTIFICATE OF CORRECTION

PATENT NO. : 7,560,920 B1
APPLICATION NO. : 11/553996
DATED : July 14, 2009
INVENTOR(S) : Tianhe Ouyang et al.

It is certified that error appears in the above-identified patent and that said Letters Patent is hereby corrected as shown below:

In Column 1, Line 13 (line 7 of references to related applications):

After "Serial Number 11/114,507" insert
-- (now U.S. Patent No. 7,301,335) --.

In Column 2, Line 48, through Column 3, line 37:

Delete entire paragraph beginning "FIG. 15 is a schematic block diagram" and ending "imaginary component 1534." and insert therefor the following paragraph:

-- Users desire probes and techniques that are large-area, fast, reliable, accurate, easy to operate, and inexpensive. There is a need to extend the conventional EC technique, as well as other eddy-current techniques, for better "noise" control (i.e., to reduce the signal changes due to variations in distance between the coils and the object being sensed) and small-flaw detection for inspection of various objects with different geometries, for example, those with flat geometry, or with approximately flat geometry in at least a local area, as well as objects with other surface geometries. In particular, there is a need to improve speed and accuracy of detection of undesirable anomalies that are near the surface of an object. --.

In Column 16, Line 54, through Column 17, line 27:

Delete entire paragraph beginning "FIG. 15 is a schematic block diagram" and ending "imaginary component 1534." and insert therefor the following paragraph, which begins on this page 2 of 4 of the Certificate of Correction, and concludes on page 3 of 4 of the Certificate of Correction:

-- FIG. 15 is a schematic block diagram of the excitation driver and sensing demodulator 1500 of apparatus 100. In some embodiments, eddy-current detection-and-display system 101 includes a sine-wave and cosine-wave generator 1520 that outputs sine and cosine versions of a wave having a selected frequency useful for scanning the object 99 (e.g., selected for the type of metal and its configuration and thickness). In some embodiments, the cosine($\omega$t) signal 1521 is buffered through adjustable amplifier 1523 having an amplification factor A, and the resulting signal A*cosine($\omega$t) is connected through an impedance (such as the resistance 1540 shown, or another suitable impedance such as one including resistance, capacitance, and/or inductance) to a selected coil 129 through analog switch 122 and/or mux 121, and the selected coil 129 is also connected to one input of differential amplifier 1528. In some embodiments, the cosine($\omega$t) signal is also buffered through adjustable amplifier 1524 having an amplification factor B, and the resulting signal B*cosine($\omega$t) is connected through an impedance (such as the resistance 1541 shown, or another suitable impedance such as one including resistance, capacitance, and/or inductance) to a selected reference coil 125 through analog switch 122 (and/or a mux, not shown), and the reference coil 125 is also connected to one input of differential amplifier 1528. The differential amplifier outputs a difference signal that represents the

CERTIFICATE OF CORRECTION (continued)
U.S. Pat. No. 7,560,920 B1

Continued from page 1:

difference between the selected sense coil 129 and the selected reference coil 125 (e.g., difference signal 1593 = E * cosine(ωt+α)). The difference signal is mixed (i.e., multiplied) by demodulator 1525 with the cosine(ωt) signal 1521 (e.g., in some embodiments, with resulting after demodulation signal Xm 1594 = cosine(ωt) * (E * cosine(ωt+α)) = ½ E * (cosine(2ωt+α) + cosine α)), then goes through low-pass filter 1526 (e.g., in some embodiments, with resulting after low-pass filter signal Xp 1596 = K * cosine(α), where, in some embodiments, K = ½ E) and H gain amplifier 1527 (e.g., in some embodiments, with resulting after horizontal gain amplifier signal X 1598 = Kh * Xp (where Kh is the horizontal gain)), and represents the real component of a signal having real and imaginary components based on the phase and amplitude changes of the selected sense coil 129. The difference signal is also mixed (i.e., multiplied) by demodulator 1535 with the sine(ωt) signal 1522 (e.g., in some embodiments, with resulting after demodulation signal Ym 1595 = sine(ωt) * (E * cosine(ωt+α)) = ½ E* (sine(2ωt+α) + sine(α))), then goes through low-pass filter 1536 (e.g., in some embodiments, with resulting after low-pass filter signal Yp 1597 = K * sine(α), where, in some embodiments, K = ½ E) and V gain amplifier 1537 (e.g., in some embodiments, with resulting after vertical gain amplifier signal Y 1599 = Kv * Yp (where Kv is the vertical gain)), and represents the imaginary component of a signal having real and imaginary components based on the phase and amplitude changes of the selected sense coil 129. These two signals are then processed by rotator 1538 which has input factors cosine(beta) and sine(beta) that are used to rotate the signals by an angle (beta), which are then output as real component 1533 and imaginary component 1534. --.

In Column 25, Line 28 (line 9 of claim 9):

Delete "E*cosine(ω+α)" and insert

-- E*cosine(ωt+α) -- therefor.

In Column 25, Lines 35-36 (lines 16-17 of claim 9):

Delete "E*cosine(ω+α)" and insert

-- E*cosine(ωt+α) -- therefor.

Signed and Sealed this

Ninth Day of February, 2010

David J. Kappos
*Director of the United States Patent and Trademark Office*